United States Patent
Barrus et al.

(10) Patent No.: US 12,403,015 B2
(45) Date of Patent: Sep. 2, 2025

(54) EXPANDABLE IMPLANT WITH WORM GEAR

(71) Applicant: K2M, Inc., Leesburg, VA (US)

(72) Inventors: Michael Barrus, Redondo Beach, CA (US); Clint Boyd, Leesburg, VA (US); Liam Patrick Barnes, Leesburg, VA (US); Jason Noel Gantick, Purcellville, VA (US); Todd M. Wallenstein, Ashburn, VA (US); Megan E. Carnes, Leesburg, VA (US)

(73) Assignee: K2M, Inc., Leesburg, VA (US)

( * ) Notice: Subject to any disclaimer, the term of this patent is extended or adjusted under 35 U.S.C. 154(b) by 141 days.

(21) Appl. No.: 17/917,755

(22) PCT Filed: Apr. 7, 2021

(86) PCT No.: PCT/US2021/026189
§ 371 (c)(1),
(2) Date: Oct. 7, 2022

(87) PCT Pub. No.: WO2021/207364
PCT Pub. Date: Oct. 14, 2021

(65) Prior Publication Data
US 2023/0165687 A1 Jun. 1, 2023

Related U.S. Application Data

(60) Provisional application No. 63/006,278, filed on Apr. 7, 2020.

(51) Int. Cl.
*A61F 2/44* (2006.01)
*A61F 2/30* (2006.01)

(52) U.S. Cl.
CPC ............ *A61F 2/4455* (2013.01); *A61F 2002/30367* (2013.01); *A61F 2002/3052* (2013.01);
(Continued)

(58) Field of Classification Search
CPC .......... A61F 2/4455; A61F 2002/30367; A61F 2002/3052; A61F 2002/30525; A61F 2002/30579; A61F 2002/30784
(Continued)

(56) References Cited

U.S. PATENT DOCUMENTS 8,303,663 B2   11/2012   Jimenez et al.
8,574,300 B2 *  11/2013   McManus ............... A61F 2/44
                                              623/17.11
(Continued)

FOREIGN PATENT DOCUMENTS

WO   2009064787 A2   5/2009
WO   2013158294 A1   10/2013

OTHER PUBLICATIONS

International Search Report including Written Opinion for PCT/US2021/026189 issued Jul. 20, 2021; 12 pages.

*Primary Examiner* — Jessica Weiss
(74) *Attorney, Agent, or Firm* — Lerner David LLP

(57) ABSTRACT

An expandable device comprising, a body defining a bore, a shaft received in the bore of the body, an end plate coupled to the shaft, wherein rotation of the shaft translates the end plate with respect to the body, and a locking mechanism engaged with the shaft so as to permit the shaft to rotate in a first direction and apply a resistance force to resist the shaft when attempting to rotate in a second direction.

20 Claims, 21 Drawing Sheets

(52) U.S. Cl.
CPC .............. *A61F 2002/30525* (2013.01); *A61F 2002/30579* (2013.01); *A61F 2002/30784* (2013.01)

(58) Field of Classification Search
USPC .......................................... 623/17.11–17.16
See application file for complete search history.

(56) References Cited

U.S. PATENT DOCUMENTS

| | | |
|---|---|---|
| 8,636,746 B2 | 1/2014 | Jimenez et al. |
| 8,992,620 B2 | 3/2015 | Ashley et al. |
| 10,420,654 B2 | 9/2019 | Logan et al. |
| 2011/0015747 A1* | 1/2011 | McManus ................. A61F 2/44 623/17.16 |
| 2011/0160861 A1* | 6/2011 | Jimenez ................ A61F 2/4455 623/17.16 |
| 2012/0158071 A1* | 6/2012 | Jimenez .................. A61F 2/447 606/86 A |
| 2015/0094814 A1* | 4/2015 | Emerick ............... A61F 2/4455 623/17.16 |
| 2017/0119542 A1* | 5/2017 | Logan .................. A61F 2/4465 |

* cited by examiner

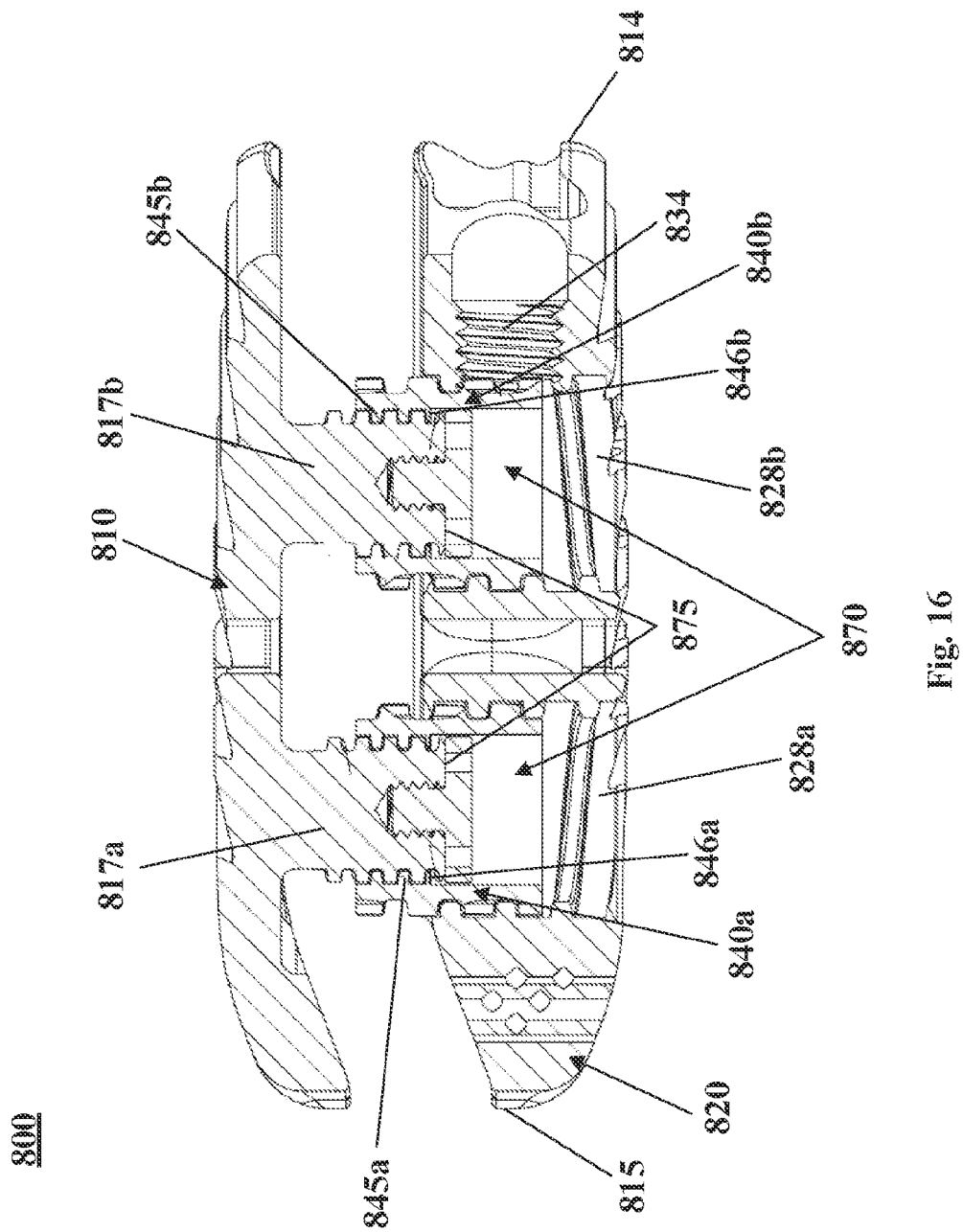

EXPANDABLE IMPLANT WITH WORM GEAR

CROSS-REFERENCE TO RELATED APPLICATIONS

The present application is a national phase entry under 35 U.S.C. § 371 of International Application No. PCT/US2021/026189, filed on Apr. 7, 2021, which claims the benefit of the filing date of U.S. Provisional Application No. 63/006,278, filed Apr. 7, 2020, entitled Expandable Implant With Worm Gear, the disclosures of which are hereby incorporated herein by reference.

BACKGROUND

Intervertebral fusion procedures involve removing at least a portion of a spinal disc between two vertebrae and implanting an intervertebral device between the two vertebrae. One example of an intervertebral device may include an expandable fusion device that can be inserted into an intervertebral space with a low profile and then expanded. Such a device can provide for a more minimally invasive surgical approach and may ease the insertion of the device between the vertebrae. Expandable fusion devices may also provide a distraction force between the two vertebrae. In this manner, the expandable fusion device can expand the vertebral foramen and prevent compression of the adjacent nerves, as well as aiding in fusing the adjacent vertebrae (such as by housing a bone growth material).

However, such expandable devices may include the risk of over-expanding the vertebral disc and compressing other portions of the spine. Moreover, the expandable device may include the risk of collapsing after implantation, creating instability within the spine and leading to improper intervertebral fusion. Additionally, expanding the expandable device can require a great deal of force given the weight compressing on the intervertebral device small enough to fit between two vertebrae. Therefore, further improvements are desirable.

BRIEF SUMMARY

In accordance with an aspect of the disclosure, an expandable device comprising, a body defining a bore, a shaft received in the bore of the body, an end plate coupled to the shaft, wherein rotation of the shaft translates the end plate with respect to the body, and a locking mechanism engaged with the shaft so as to permit the shaft to rotate in a first direction and apply a resistance force to resist the shaft when attempting to rotate in a second direction. At least one of the end plate and the body may include a textured surface. At least one of the end plate and the body may include a plurality of pores. The end plate may define an opening and the body defines an opening, the opening of the end plate being in communication with the opening of the body. The body may define a first opening transverse to the bore, the device further comprising a first gear sleeve threadably received in the first threaded opening of the body. The first gear sleeve may define a channel, the end plate including a first post received in the channel of the first gear sleeve. The first gear sleeve may include gear teeth, the shaft having a first threaded section engaged with the gear teeth. The expandable may further comprise a pin, wherein the body defines a hole configured to receive the pin. The shaft may define an indent configured to engage with the pin such that the worm gear is axially fixed to the body. The expandable device may further comprise a spring applying a spring force to the locking mechanism. The shaft may include a cap at an end of the shaft, the cap configured to engage the locking mechanism. The cap may be tapered with a first taper angle and the locking mechanism may be tapered with a second taper angle, the second taper angle being more acute than the first taper angle such that the locking mechanism applies the resistance force to the cap when the locking mechanism is engaged to the cap. The cap may have a first ratchet teeth and the locking mechanism may have a second ratchet teeth configured to engage the first ratchet teeth, the second ratchet teeth applying the resistance force to the first ratchet teeth. The bore may include a first section and a second section, the first section configured to receive the cap and the second section configured to receive the body, the first section having a first diameter and the second section having a second diameter, the first diameter being larger than the second diameter. The locking mechanism may include an extension and the first section may include a first portion radially extending from the first section, the first portion configured to receive the extension such that the locking mechanism is rotationally fixed within the first section. The locking mechanism may include a pawl having a ratchet tooth configured to engage teeth on the worm gear. The expandable may further comprise a ball bearing configured to engage with the gear teeth of the first gear sleeve. The body may include a second opening, the expandable device may further comprise a second gear sleeve received in the second opening, the second gear sleeve having gear teeth and defining a channel therethrough, the end plate may have a second post received in the channel of the second gear sleeve, and the shaft may have a second threaded section engaged with the gear teeth of the second gear sleeve.

In accordance with another aspect of the disclosure, an expandable device comprising, a body defining a bore and a first opening transverse to the bore, a shaft received in the bore of the body, a first gear sleeve received in the first opening and defining a channel, the first gear sleeve having a stopping structure within the channel, an end plate having a first post received in the channel of the first gear sleeve, and a stop plate engaged with the first post and received in the channel, wherein rotation of the shaft translates the end plate to a maximum distance determined by the engagement between the stop plate and the stopping structure. The post of the end plate may define a threaded opening and the stop plate may include a post, the post of the stop plate received in the threaded opening of the post of the end plate. The stop plate may define a hole radially distant from an axis defined by the post and configured to receive a set screw. The channel of the first gear sleeve may define a first threaded section configured to receive the post of the end plate and a second section configured to receive the stop plate. The stopping structure may lie between the first threaded section and the second section. At least one of the end plate and the body may include a textured surface. At least one of the end plate and the body may include a plurality of pores. The end plate may define an opening and the body may define an opening, the opening of the end plate being in communication with the opening of the body. The first gear sleeve may include gear teeth, the shaft having a first threaded section engaged with the gear teeth. The body may include a second opening, the expandable device may further comprise a second gear sleeve received in the second opening, the second gear sleeve having gear teeth and defining a channel therethrough, the end plate may have a second post received in the channel of the second gear sleeve, and the shaft may have a second threaded section engaged with the gear teeth of the second gear sleeve. The expandable may further comprise a pin, wherein the body may define a hole configured to receive the pin. The shaft may define an indent configured to engage with the pin such that the worm gear is axially fixed to the body.

In accordance with another aspect of the disclosure, a method of using an expandable device having a body, comprising, rotating a shaft in a first rotational direction within the body to translate an end plate in a first axial direction, and locking the end plate in a first position along the first axial direction by engaging the shaft with a locking mechanism applying a resistance force to the shaft to resist the shaft from rotating in a second rotational direction opposite the first rotational direction. The method may further comprise, after locking the end plate, further rotating the worm gear in the second rotational direction by applying a rotation force greater than the resistance force. The shaft may include a taper having a first angle and the locking mechanism may have an opening having a taper with a second angle, the second angle being more acute than the first angle, wherein locking the end plate may include the resistance force being applied from the taper of the shaft being received in the opening of the locking mechanism. The method may further comprise unlocking the end plate by applying a pushing force to the shaft to separate the taper of the shaft and the opening of the locking mechanism. The shaft may include ratchet teeth and the locking mechanism may include ratchet teeth, wherein locking the end plate may include the resistance force being applied from the ratchet teeth of the locking mechanism engaging with the ratchet teeth of the shaft. The method may further comprise unlocking the end plate by applying a pushing force to the locking mechanism to disengage the ratchet teeth of the locking mechanism and the ratchet teeth of the shaft. The expandable device may include a spring applying a spring force to the locking mechanism, wherein applying the pushing force may include the pushing force being greater than the spring force. The method may further comprise rotating the shaft in the second rotational direction so as to further translate the end plate in a second axial direction opposite the first axial direction. The method may further comprise locking the end plate in a second position by engaging the shaft with the locking mechanism applying the resistance force to the shaft. Rotating the shaft may include axially fixing the shaft with a pin received in an indent of the shaft while the shaft rotates. The method may further comprise inserting an actuating mechanism within an opening of the shaft. The method may further comprise inserting an inserter within a second threaded opening of the body. The method may further comprise inserting a bone growth material within at least one of an opening or pores within at least one of an end plate or body. The method may further comprise rotating a first gear sleeve within a first opening of the body and about a first post of the end plate, the first gear sleeve defining a channel threadably receiving the first post. The method may have a first threaded section and the first gear sleeve may have gear teeth engaged with the first threaded section, and wherein rotating the shaft further rotates the first gear sleeve due to engagement between the first threaded section of the shaft and the gear teeth of the first gear sleeve. The body may include a second opening, the expandable device further comprises a second gear sleeve threadably received in the second opening, the second gear sleeve having gear teeth and a defining a channel therethrough, the end plate may have a second post received in the channel of the second gear sleeve, the shaft may have a second threaded section engaged with the gear teeth of the second gear sleeve, and the method may further comprise, rotating the second gear sleeve within the second opening of the body and about the second post of the end plate.

In accordance with another aspect of the disclosure, a method of using an expandable device having a body, comprising, rotating a shaft within the body in a first rotational direction about a longitudinal axis of the shaft so as to rotate a first gear sleeve about an axis extending in a first axial direction transverse to the longitudinal axis, the rotation of the first gear sleeve causing a post connected to an end plate to translate respect to the first gear sleeve along the first axial direction, the first gear sleeve defining a channel receiving the post of the end plate therein, and stopping the translation of the end plate by engaging a stop plate coupled to the post with a stopping structure of the first gear sleeve. The channel of the first gear sleeve may define a first threaded section and a second section, the stopping structure being in between the first threaded section and the second section, wherein the first post of the end plate is received through the first threaded section and the stop plate is received in the second section, wherein translating the end plate may include translating the post of the end plate within the first threaded section and translating the stop plate within the second section. Rotating the shaft may include axially fixing the shaft with a pin received in an indent of the shaft while the shaft rotates. The method may further comprise inserting an actuating mechanism within an opening of the shaft. The method may further comprise inserting an inserter within a second threaded opening of the body. The method may further comprise inserting a bone growth material within at least one of an opening or pores within at least one of an end plate or body. The shaft may have a first threaded section and the first gear sleeve may have gear teeth engaged with the first threaded section, and wherein rotating the shaft further rotates the first gear sleeve due to engagement between the first threaded section of the shaft and the gear teeth of the first gear sleeve. Rotating the shaft within the body in the first rotational direction may drive a second gear sleeve to rotate about a second axis extending in the first axial direction, the rotation of the second gear sleeve causing a second post connected to the end plate to translate along the first axial direction within a channel of the second gear sleeve.

BRIEF DESCRIPTION OF THE DRAWINGS

These and other features, aspects, and advantages of the present invention will become better understood with regard to the following description, and accompanying drawings.

FIG. 16 depicts a cross-sectional view of the expandable device of FIG. 14 in an expanded condition.

DETAILED DESCRIPTION

When referring to specific directions and planes in the following disclosure, it should be understood that, as used herein, the term "proximal" means closer to the operator/surgeon, and the term "distal" means further away from the operator/surgeon. The term "anterior" means toward the front of the body or the face, and the term "posterior" means toward the back of the body. With respect to the longitudinal axis of the spine, the term "superior" refers to the direction towards the head, and the term "inferior" refers to the direction towards the pelvis and feet. The "transverse plane" is that plane which is orthogonal to the longitudinal axis of the spine. The "coronal plane" is a plane that runs from side to side of the body along the longitudinal axis of the spine and divides the body into anterior and posterior portions. The "sagittal plane" is a plane that runs along the longitudinal axis of the spine and defines a plane of symmetry that separates the left and right sides of the body from each other. Finally, the "medial" refers to a position or orientation toward the sagittal plane, and lateral refers to a position or orientation relatively further from the sagittal plane.

Figure 1:
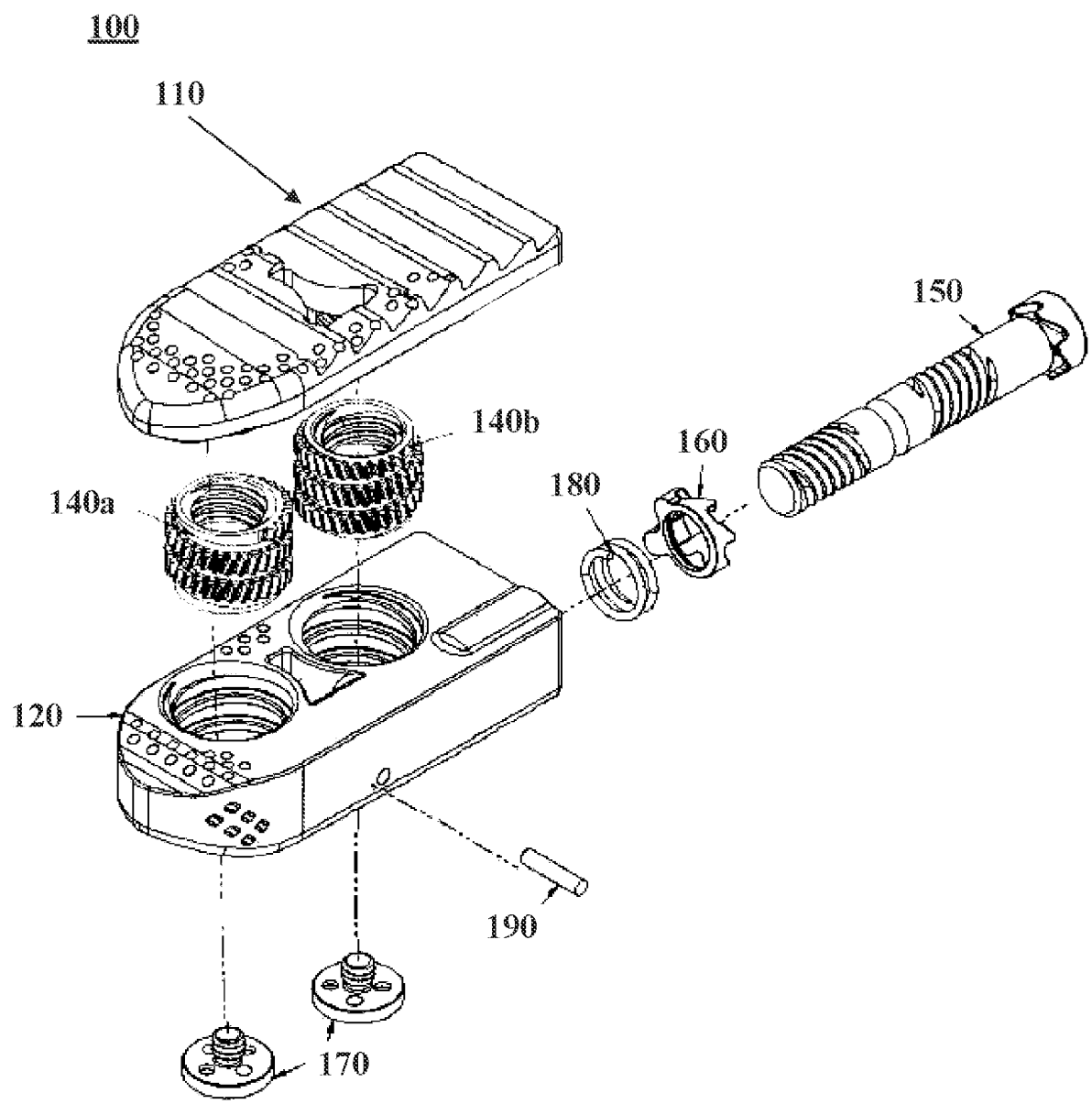
FIG. 1 depicts an exploded view of an expandable device according to one embodiment of the disclosure.

FIG. 1 depicts an exploded view of an expandable device 100. Device 100 expands toward an expanded condition when end plate 110 is further away from body 120 and collapses towards a collapsed condition when the end plate is closer to the body.

As discussed further below, right-hand gear sleeve 140a and left-hand gear sleeve 140b threadably receive end plate 110 while body 120 threadably receives the gear sleeves. As a result, rotation of the gear sleeves within the body creates a telescoping expansion in which the gear sleeves translate relative to the body and the plate translates relative to the gear sleeves (and, in turn, the body), similar to that disclosed in U.S. Pat. No. 8,303,663 ("the '663 Patent"), the entire disclosure of which is hereby incorporated herein by reference. Worm gear (or shaft) 150 is received within body 120, being axially held in place by pin 190 received within the body, and is threadably engaged with gear sleeves 140a,b such that rotation of the worm gear rotates the gear sleeves. A maximum translating distance is set by contact between stop posts 170 and gear sleeves 140a,b. Locking mechanism 160 is received in body 120 such that the locking mechanism is rotationally fixed relative to worm gear 150. In this manner, the ratcheting engagement between locking mechanism 160 and worm gear 150 allows for the worm gear to rotate in one direction but not the other, thereby preventing back driving of the worm gear. Spring 180 applies a spring force to locking mechanism 160 and worm gear 150 such that locking mechanism 160 can passively maintain engagement with worm gear 150.

Figure 2A:
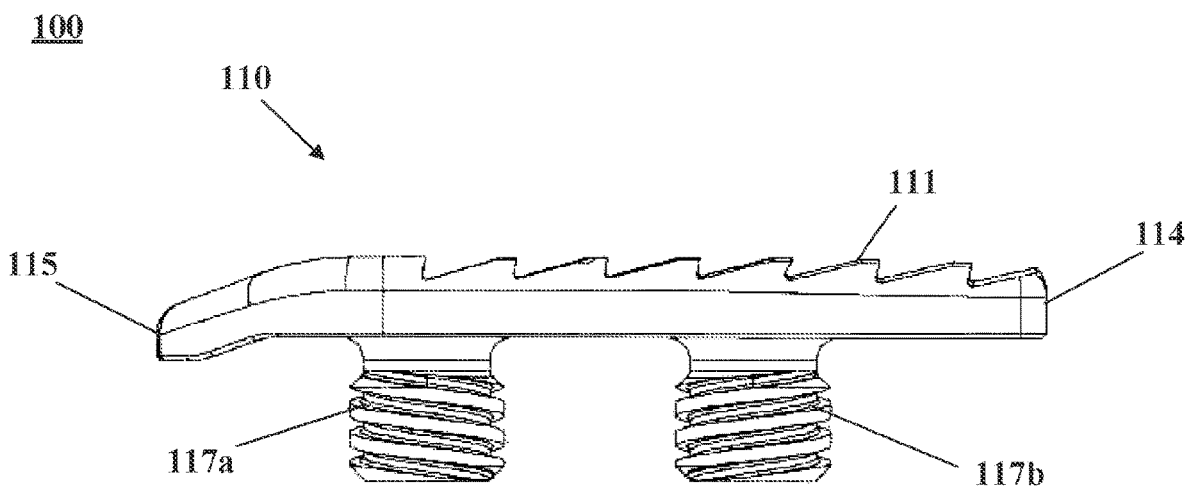
FIG. 2A depicts a side view of an end plate of the expandable device of FIG. 1.
Figure 2B:
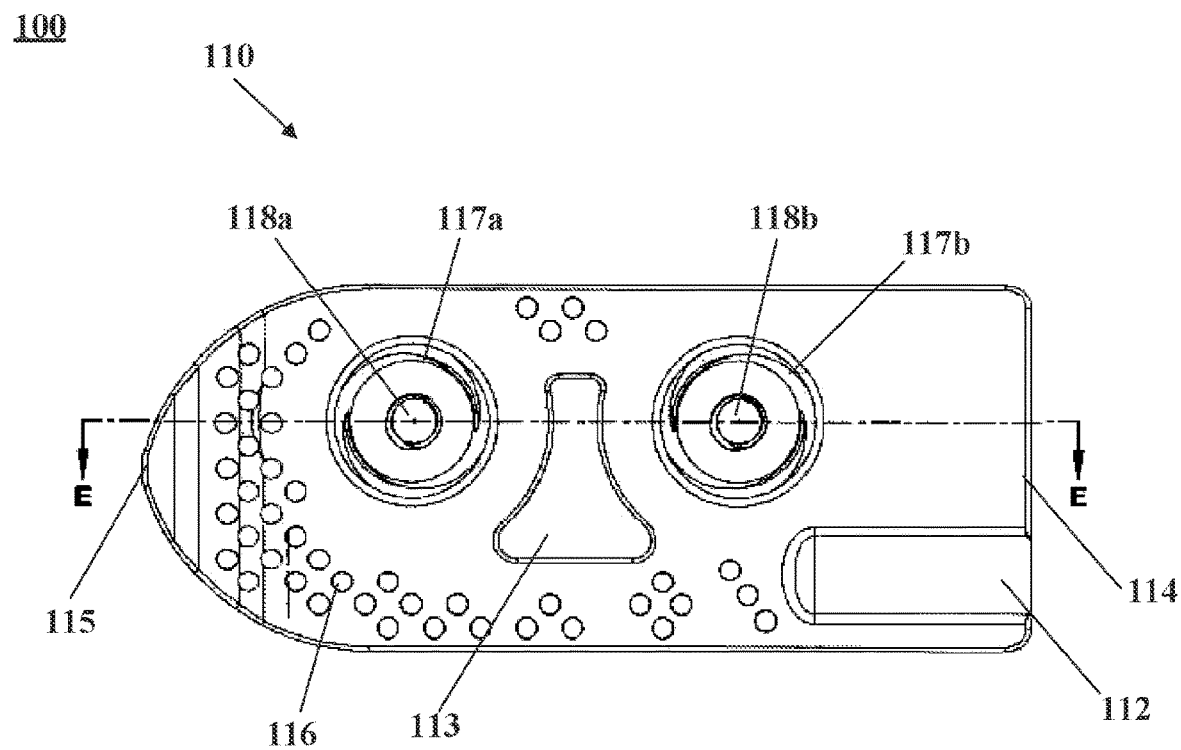
FIG. 2B depicts a top view of the end plate of FIG. 2A.
Figure 2C:
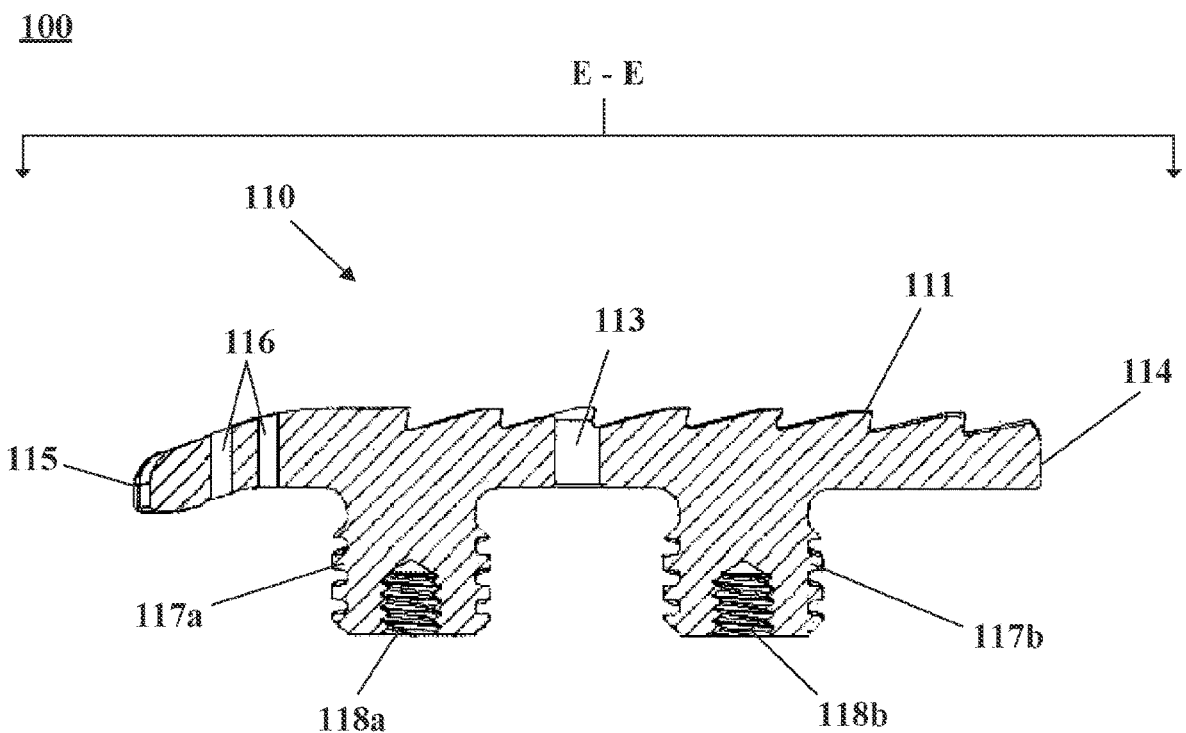
FIG. 2C depicts a cross-sectional view of the end plate of FIG. 2A along the E-E axis.

FIGS. 2A-2C depicts end plate 110 having a proximal end 114 and a distal end 115. End plate 110 is configured to interface with an adjacent vertebra. Recess 112 is positioned adjacent to proximal end 114 and is configured to receive protrusion 122 of body 120 shown in FIGS. 3A-3E when device 100 is in a collapsed condition. Although distal end 115 is depicted as being inferiorly angled to allow for easier insertion into an intervertebral space, in alternative embodiments, end plate 110 may be substantially planar along its entire length.

End plate 110 has a textured surface 111 with ridges shaped to better generate friction and prevent slippage with an adjacent vertebra. As shown in the figures, the ridges may be substantially triangular, and each ridge may be asymmetric on its proximal and distal sides. For example, the distal side of each ridge may be sloped gently with respect to the adjacent vertebral surface, while the proximal side of each ridge may be more sharply angled with respect to the vertebral surface. Such an arrangement may make it easier to insert the device 100 distally into the intervertebral space, while resisting proximal movement. In other embodiments, however, the ridges may be symmetrical on their proximal and distal sides, such as shown in FIGS. 1A-1C of the '663 Patent. Alternatively, end plate 100 may have a generally smooth surface, or alternative textured surfaces, such as an etched surface, a scored surface or a notched surface.

End plate 110 includes pores 116 extending therein or therethrough to facilitate bone ingrowth. In addition, or alternatively, opening 113 may be provided, which communicates with the interior of the device 100, including opening 123 of body 120 shown in FIG. 3C. In that way, bone graft material provided inside device 100 may communicate with the adjacent vertebral bodies to facilitate bone growth over time. Alternatively, end plate 100 may be solid with no openings 113 or pores 116, or include only one of the opening or pores.

Posts 117a,b extend from end plate 110 on an opposite side of the end plate to textured surface 111. Posts 117a,b are configured to be respectively received in gear sleeves 140a, b, as depicted in FIGS. 1 and 4A-4D. Posts 117a,b have an exterior threaded surface configured to engage with a threaded section of a channel defined within gear sleeves 140a,b such that the gear sleeves are rotatably engaged with the posts. Thus, rotation of the gear sleeves causes the posts to telescopically translate in a superior or inferior direction with respect to the gear sleeves as the gear sleeves translate with respect to the body 120. Further, posts 117a,b of end plate 110 each have an internal threaded surface in threaded openings 118a,b, as depicted in FIG. 2C, configured to receive stop post 172 of stop plate 170 depicted in FIGS. 7A and 7C such that the contact between the stop plate and gear sleeves 140a,b prevents end plate 110 from expanding too far. The external threads of post 117a are left-hand threaded while the external threads of post 117b are right-hand threaded. It is believed that such an arrangement can allow for a greater distraction force to be applied to the adjacent vertebra, as well as a decreased amount of friction between the posts and the gear sleeves when expanding and collapsing device 100. However, in alternative embodiments, the external threading may be switched, or both posts 117a,b may have the same threading direction.

FIGS. 3A-3G depict body 120 having a proximal end 124 and a distal end 125 with a textured surface 121 similar to textured surface 111 of end plate 110. Body 120 includes threaded openings 128a,b configured to receive posts 117a,b of end plate 110. Threaded openings 128a,b define a channel and windows 138a,b along a length of the channel. Windows 138a,b allow for threaded openings 128a,b to be in communication with second section 137 of bore 132. In this manner, when worm gear 150, shown in FIGS. 5A-5B, is received in bore 132 and gear sleeves 140a,b, shown in FIGS. 4A-4D, are respectively received in threaded openings 128a,b, threaded sections 157a,b of the worm gear can engage with gear teeth 143a,b of the gear sleeves. Although distal end 125 is depicted as being tapered in both superior-inferior and transverse planes, in alternative embodiments, the distal end of body 120 may have a substantially similar cross-sectional surface area as proximal end 124.

Body 120 has pores 126 and an opening 123 similar to pores 116 and opening 113 of end plate 110. The opening 123 may define a channel extending through the interior of the body 120. Body 120 additionally includes pores 129, 130, adjacent distal tip 125, running along a medial and lateral direction through at least a portion of the body and serving a similar purpose as pores 126 and opening 123. Pores 130 may further communicate with opening 123, for example to allow bone graft material within the opening 123 to pass through the side of the body 120. Body 120 further includes a pin hole 127 for receiving a pin 190, as depicted in FIG. 1. Alternative embodiments of body 120 may include more or fewer pores or openings, including no pores or openings.

Figure 3A:
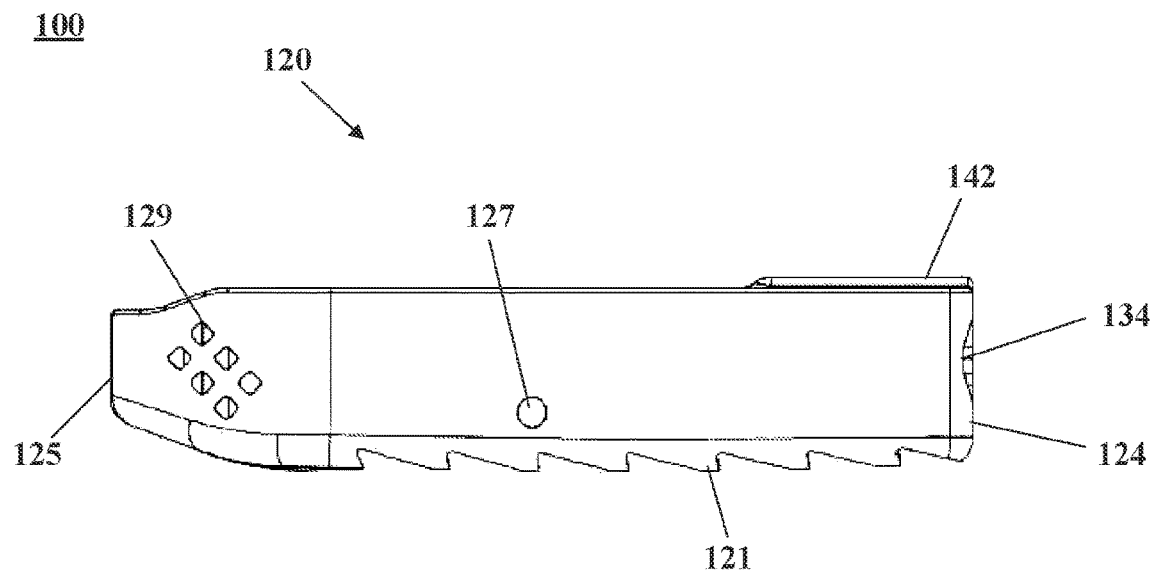
FIG. 3A depicts a first side view of a body of the expandable device of FIG. 1.
Figure 3B:
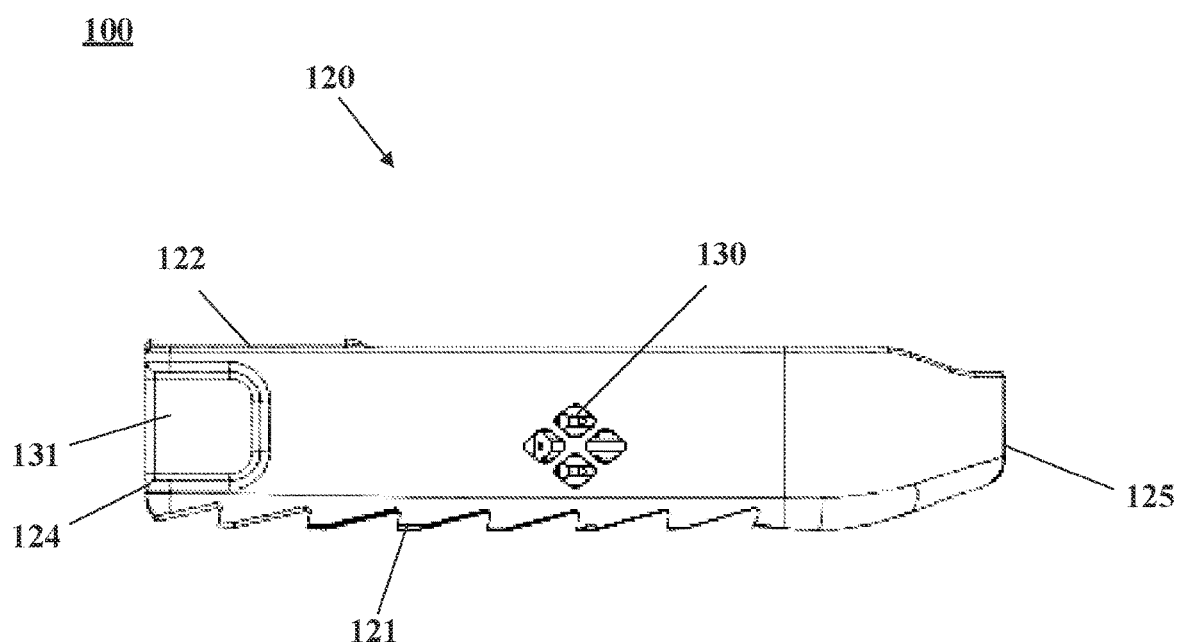
FIG. 3B depicts a second side view, opposite the first side view, of the body of FIG. 3A.
Figure 3C:
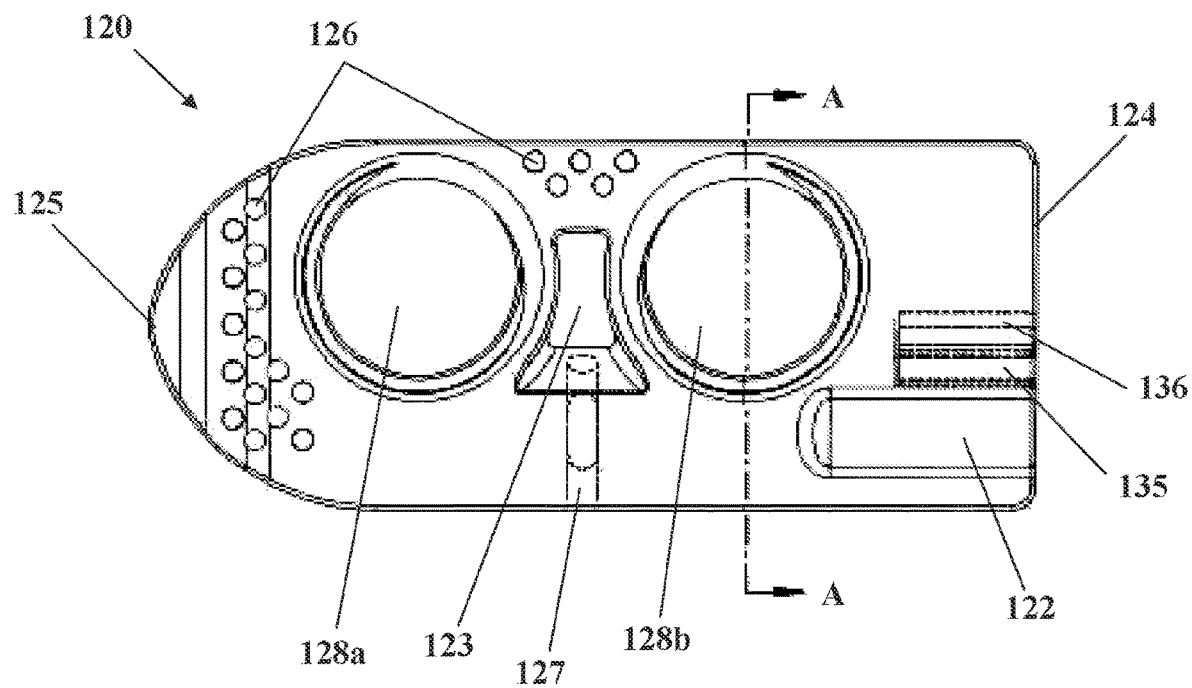
FIG. 3C depicts a top view of the body of FIG. 3A.
Figure 3D:
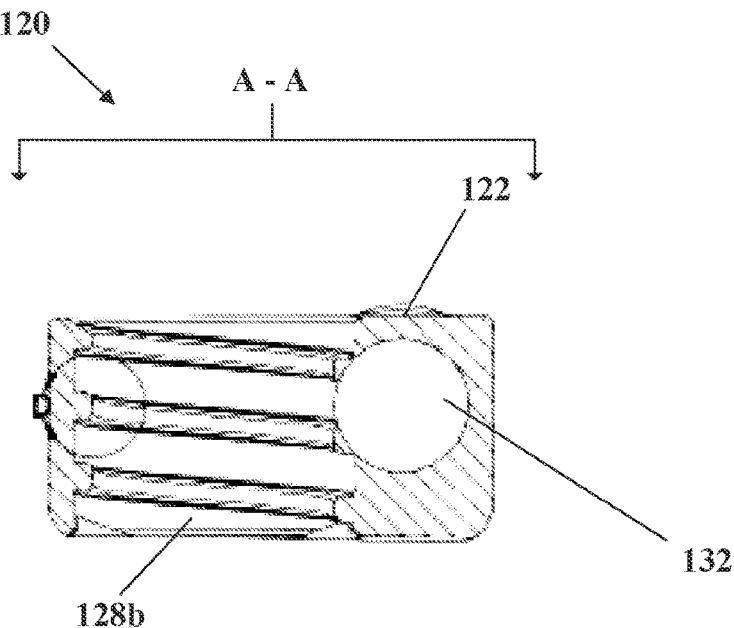
FIG. 3D depicts a cross-sectional view of the body of FIG. 3A along the A-A axis.
Figure 3E:
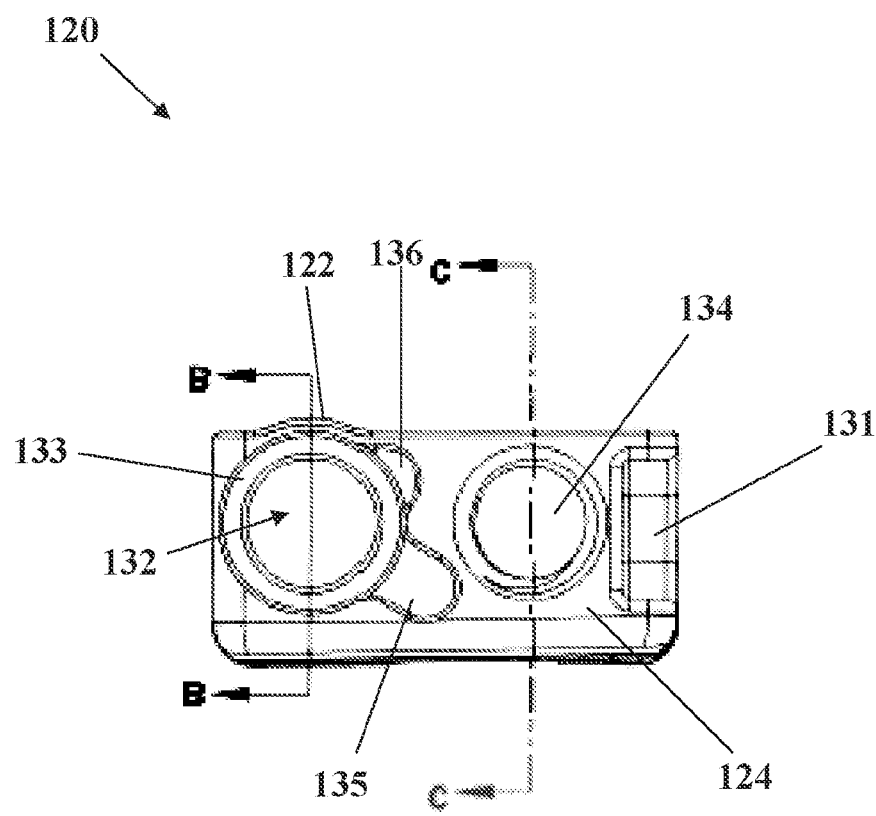
FIG. 3E depicts a rear view of the body of FIG. 3A.
Figure 3F:
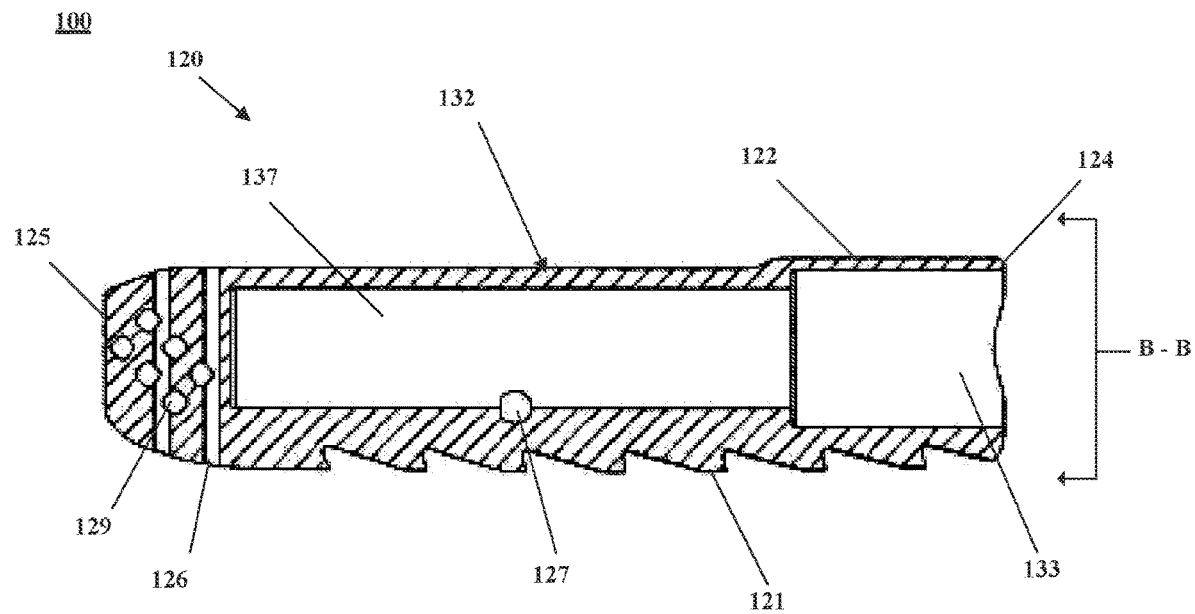
FIG. 3F depicts a cross-sectional view of the body of FIG. 3A along the B-B axis.
Figure 3G:
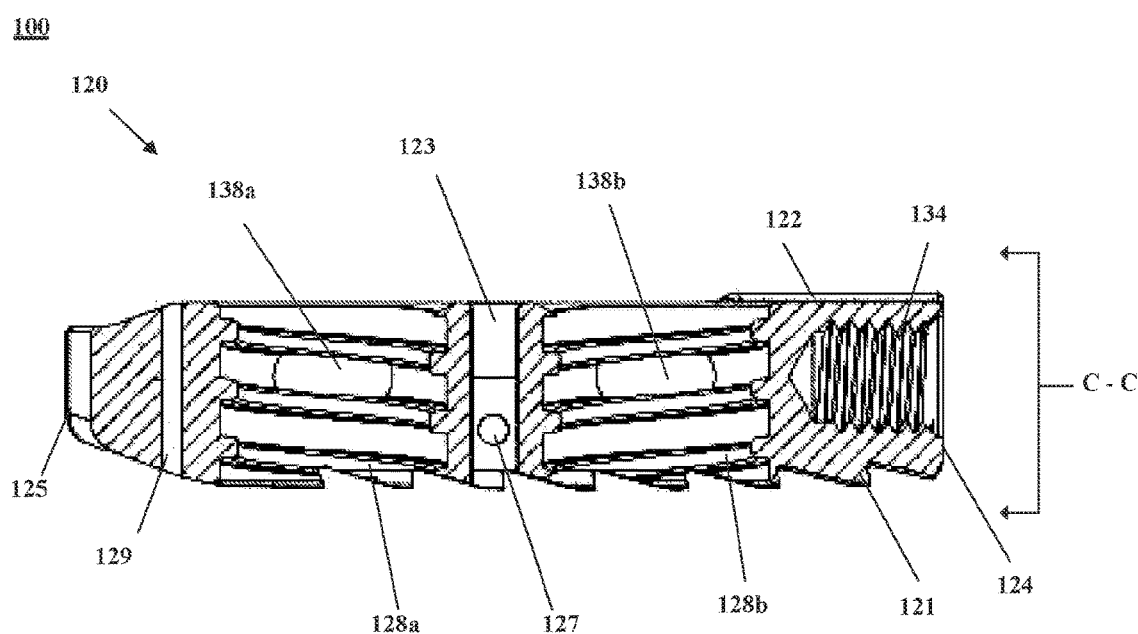
FIG. 3G depicts a cross-sectional view of the body of FIG. 3A along the C-C axis.

As shown in FIG. 3E, body 120 includes a threaded opening 134 and bore 132. Threaded opening 134 is located at proximal end 124 and configured to engage with an externally threaded portion of an inserter (not shown) such that the inserter may assist in delivering device 100 within the intervertebral space. Notch 131 is located adjacent bore threaded opening 134 and is configured to receive a protrusion (not shown) of the inserter to prevent rotation of device 100 when the device is engaged with the inserter. Bore 132 includes a first section 133 and second section 137. Second section 137 is configured to receive a body 158 of worm gear 150 shown in FIGS. 5A-5B, while first section 133 is configured to receive cap 151 of the worm gear. Although FIG. 3F depicts first section 133 having a larger diameter than second section 137, in alternative embodiments, the first section and the second can have the same diameter, or the second section can have a smaller diameter than the first section. First section is configured to receive spring 180, locking mechanism 160 and cap 151 of worm gear 150. First section 133 includes portions 135, 136 radially extending from the first section. First portion 135 and second portion 136 of first section 133 are configured to respectively receive extension 163 and extended ratchet tooth 161 of locking mechanism 160 shown in FIG. 6A. As discussed further below, the engagement between locking mechanism 160 and first section 133 allows axial movement of the locking mechanism but prevents rotation of the locking mechanism such that worm gear 150 can be rotated with respect to the locking mechanism.

FIGS. 4A-4D depicts right-hand gear sleeve 140a having a superior end 141a and an inferior end 142a, and defining a channel 145a therethrough. Right-hand gear sleeve 140a and left-hand gear sleeve 140b share the same features except the right-hand gear sleeve has opposite-handed external threads to the left-hand gear sleeve. Channel 145a includes a threaded section 148a configured to receive and threadably mate with post 117a of end plate 110 while exterior threads 144a are configured to be received in and mate with an interior thread of threaded openings 128a of body. Exterior threads 144a include gear teeth 143a cut into the exterior threads and configured to engage with thread sections 157a of worm gear 150 such that rotation of gear teeth 143a by worm gear 150 rotates gear sleeve 140a to translate in superior or inferior direction. Rotation of gear sleeve 140a also rotates the gear sleeve about post 117a of end plate 110 such that both the gear sleeve and end plate are translated relative to each other as they both translate away from body 120, thereby creating a telescopic movement to expand or collapse device 100. Although gear teeth 143a are depicted as being cut down to the root or minor diameter of exterior threads 144a, in alternative embodiments, the gear teeth may only be cut a distance between the major and minor diameter of the exterior thread to maximize the strength of both the exterior threads and gear teeth.

Figure 4A:
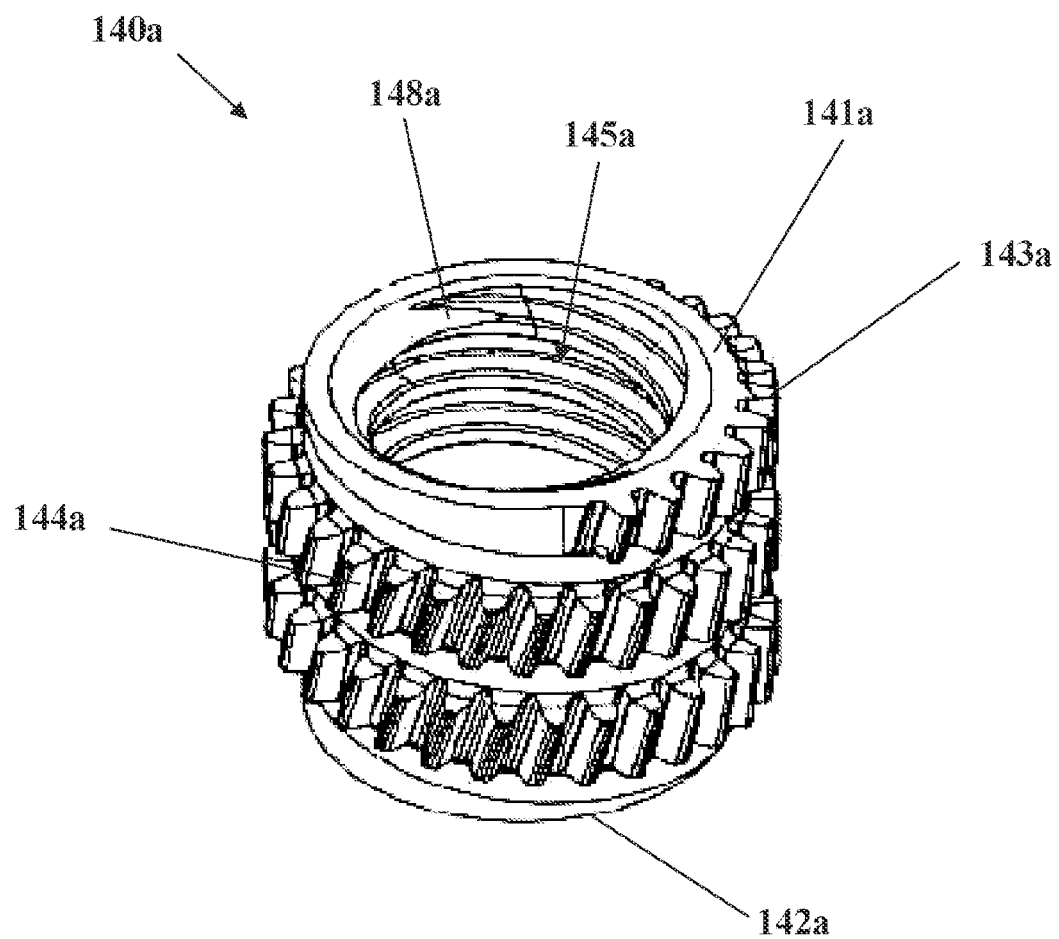
FIG. 4A depicts an isometric view of a right-handed gear sleeve of the expandable device of FIG. 1.
Figure 4B:
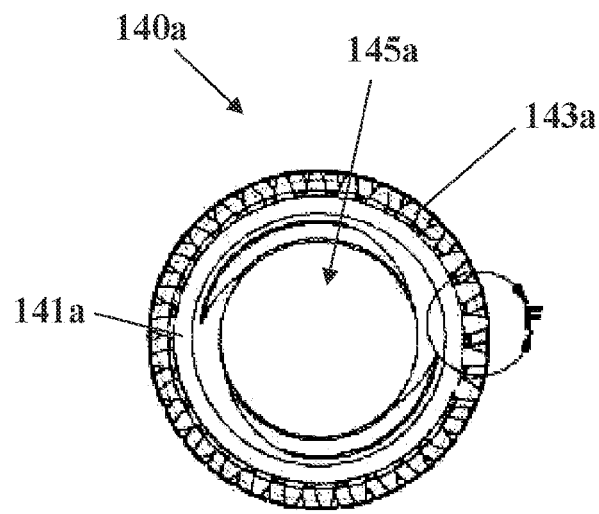
FIG. 4B depicts a top view of the right-handed gear sleeve of FIG. 4A.
Figure 4C:
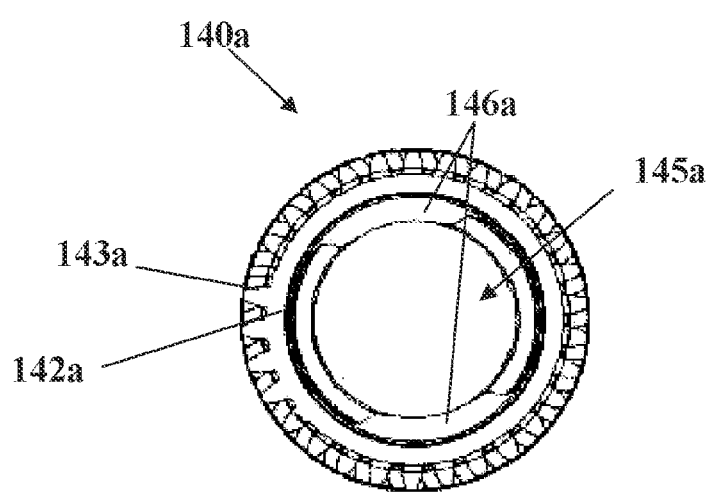
FIG. 4C depicts a bottom view of the right-handed gear sleeve of FIG. 4A.
Figure 4D:
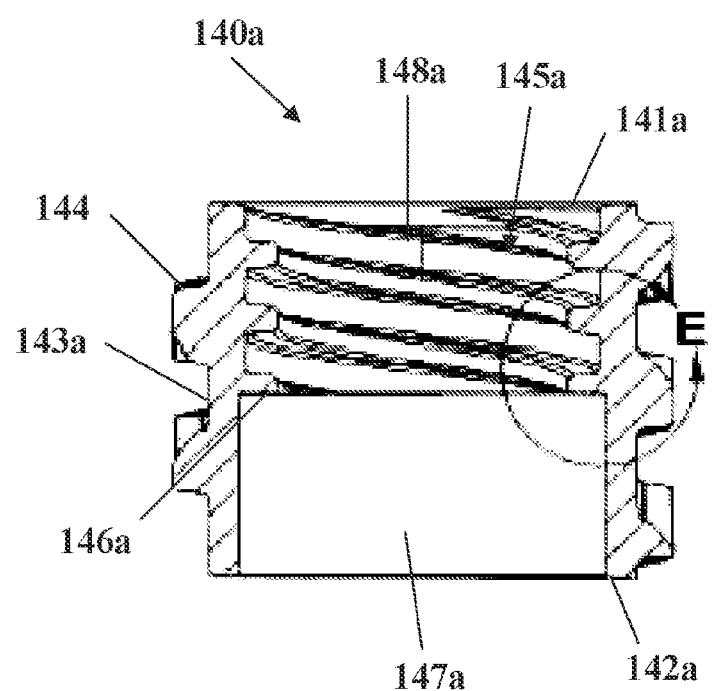
FIG. 4D depicts a cross-sectional view of the gear sleeve of FIG. 4A, sectioned by a plane extending along the rotational axis of the gear sleeve.
Figure 5A:
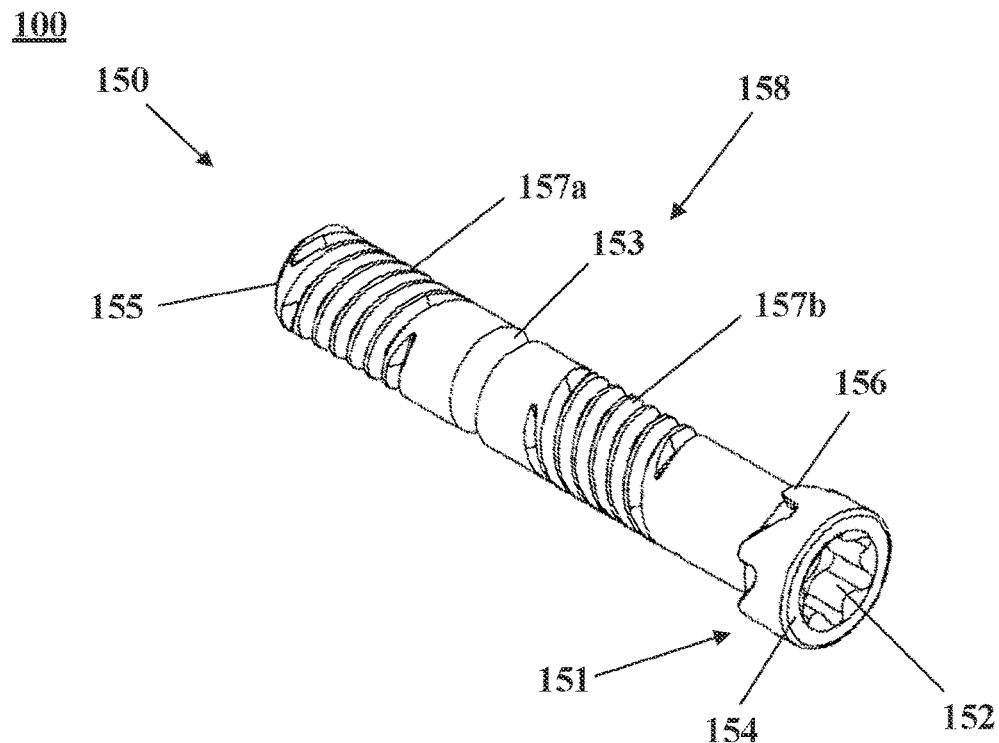
FIG. 5A depicts an isometric view of a worm gear of the expandable device of FIG. 1.
Figure 5B:
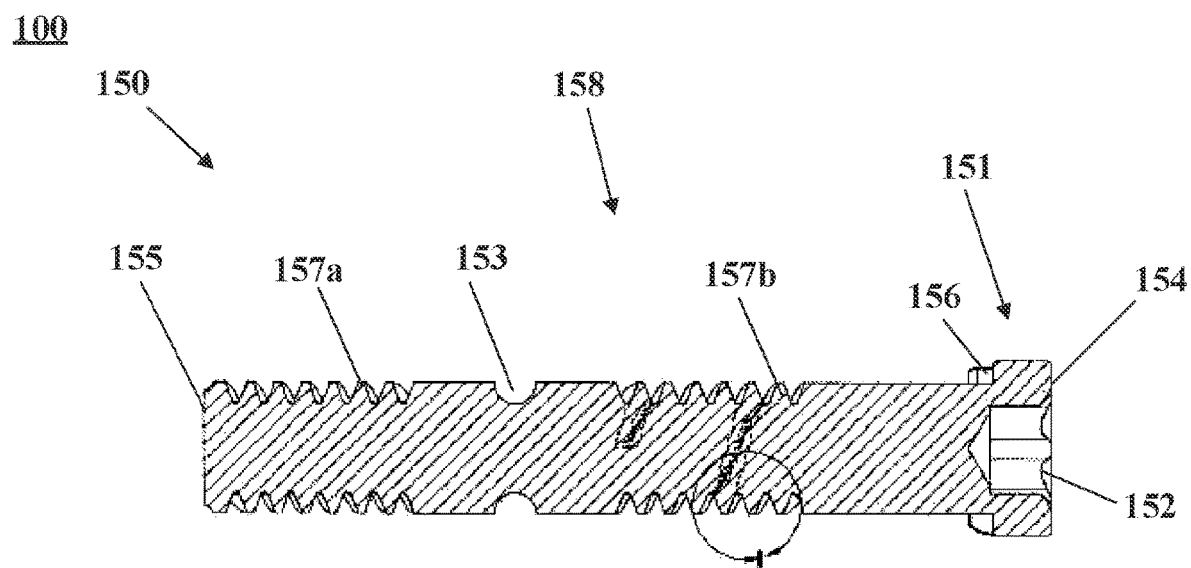
FIG. 5B depicts a cross-sectional view of the worm gear of FIG. 5A along its longitudinal axis.

As shown in FIG. 4D, threaded section 148a has a length defined between superior end 141a and ledges (or stopping structures) 146. Second portion 147a is defined within the interior of right-hand gear sleeve 140 a between ledges 146 and inferior end 142a. Second portion 147a is configured to receive stop plate 170. Ledges 146a are configured to engage with a superior surface 175 of stop cap 171 when stop plate 170 is received within gear sleeve 140a and post 117a, as described further below.

FIGS. 5A-5B depicts worm gear 150 having cap 151 at a proximal end 154 and body 158 with a distal end 155. The cap 151 may be monolithically formed with the body 158, or the cap 151 may be separately formed and joined to the body 158. As described above, cap 151 is configured to be received within first section 133 of bore 132 in body 120 while ratchet teeth 156 are configured to engage with extended ratchet tooth 161 and ratchet teeth 162 of locking mechanism 160. This ratcheting mechanism allows worm gear 150 to be rotated in a first direction but prevented from rotating in an opposite direction relative to locking mechanism 160. Cap 151 includes an opening 152 configured to be actuated by an actuation mechanism (not shown). For example, this can include a hex driver, screw driver, or the like. Worm gear 158 is axially fixed to body 120 through pin 190 being at least partially received within indent 153.

Body 158 includes thread sections 157a,b. Thread section 157a has right-hand threads configured to engage exterior threads 144a of right-hand gear sleeve 140a while thread section 157b has left-hand threads configured to engage the corresponding exterior threads of left-hand gear sleeve 140b. In this manner, rotation of cap 151 rotates body 158 which, in turn, rotates gear sleeves 140a,b, translating both the gear sleeves and end plate 110 to expand or collapse device 100. The opposite-hand engagement between thread sections 157a,b and the exterior threads of gear sleeves 140a,b is believed to decrease the amount of friction between worm gear 150 and the gear sleeves while allowing for a greater distraction force to be applied to the adjacent vertebra when expanding and collapsing device 100.

Figure 6A:
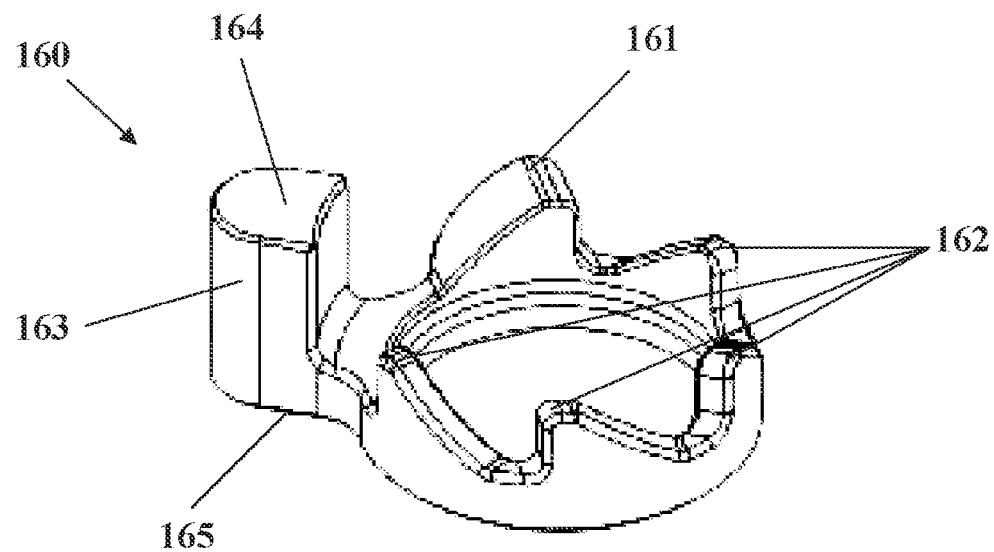
FIG. 6A depicts an isometric view of a locking mechanism of the expandable device of FIG. 1.
Figure 6B:
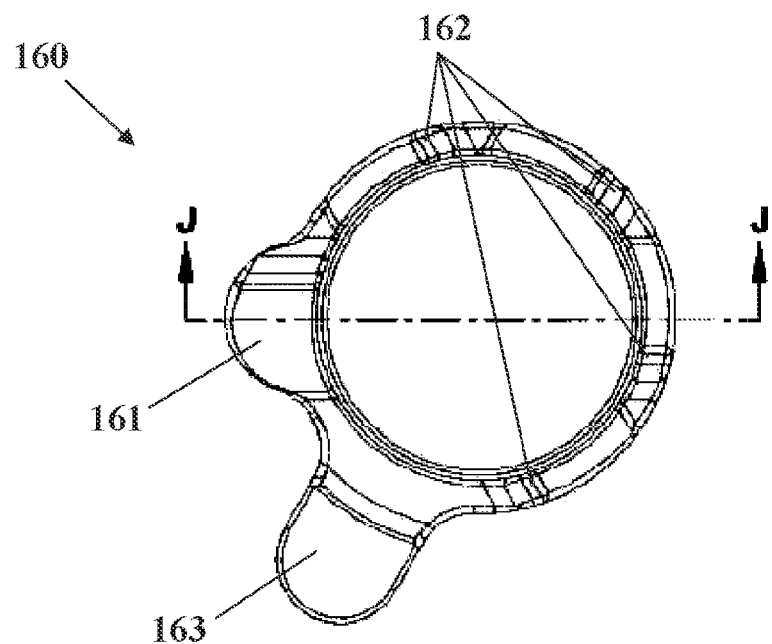
FIG. 6B depicts a top view of the locking mechanism of FIG. 6A.

FIGS. 6A-6B depicts locking mechanism 160 having ratchet teeth 162 and extension 163 defined between a proximal end 164 and a distal end 165. The proximal end 164 of extension 163 may serve as an interface for a mechanism (e.g., a pin) on the inserter to push the locking mechanism 160 distally to disengage the ratcheting engagement and allow the device to collapse, as discussed below. Extended ratchet tooth 161 is similar in structure to any teeth of ratchet teeth 162 except the extended ratchet tooth is thicker than the other ratchet teeth. Specifically, an extended portion protrudes radially outwardly from an exterior surface of extended ratchet tooth 161. As described above, locking mechanism 160 is configured to be received within first section 133 of bore 132 such that extension 163 is received within first portion 135 and extended ratchet tooth 161 is received within second portion 136. In this manner, once locking mechanism 160 and worm gear 150 are received within body 120, locking mechanism is rotationally fixed such that the worm gear can rotate relative to the locking mechanism.

Moreover, extended ratcheting tooth 161 and ratchet teeth 162 of locking mechanism 160 are configured to engage with ratchet teeth 156 of worm gear 150 in a ratchet-like manner. As such, rotation of worm gear 150 in a first, clockwise direction would allow the sloped portions of ratchet teeth 156 of the worm gear to slide along the sloped portions of ratcheting tooth 161 and ratchet teeth 162 of locking mechanism 160 while the ratchet teeth of the locking mechanism applies a resistance force to the ratchet teeth of the worm gear to prevent the worm gear from rotating in the opposite, counter-clockwise direction. In this manner, after rotation of worm gear 150 in a first direction to rotate gear sleeves 140a,b to expand end plate 100, the position of end plate 100 can be locked in place through the engagement between locking mechanism 160 and cap 151 of the worm gear. In this manner, once device 100 has been expanded to a desired position, the engagement between locking mechanism 160 and worm gear 150 prevents the worm gear from back driving and unintentionally collapsing the device.

Figure 7A:
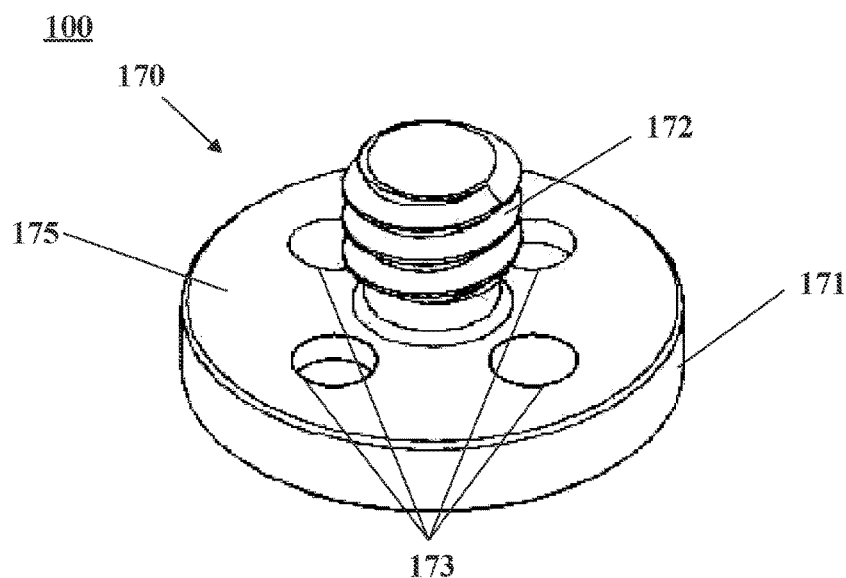
FIG. 7A depicts an isometric view of a stop plate of the expandable device of FIG. 1.
Figure 7B:
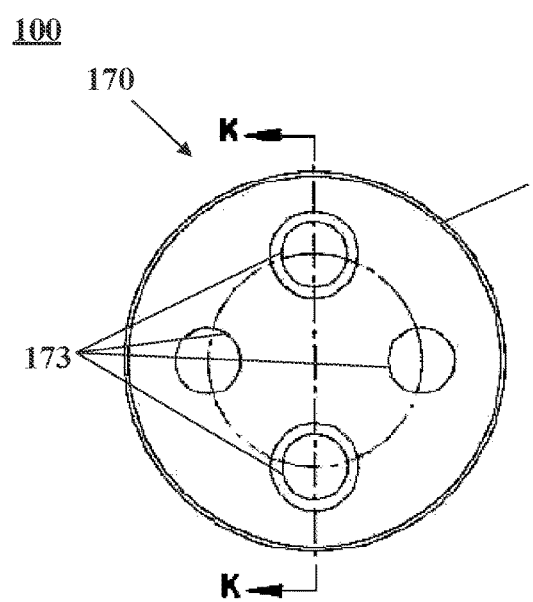
FIG. 7B depicts a bottom view of the stop plate of FIG. 7A.
Figure 7C:
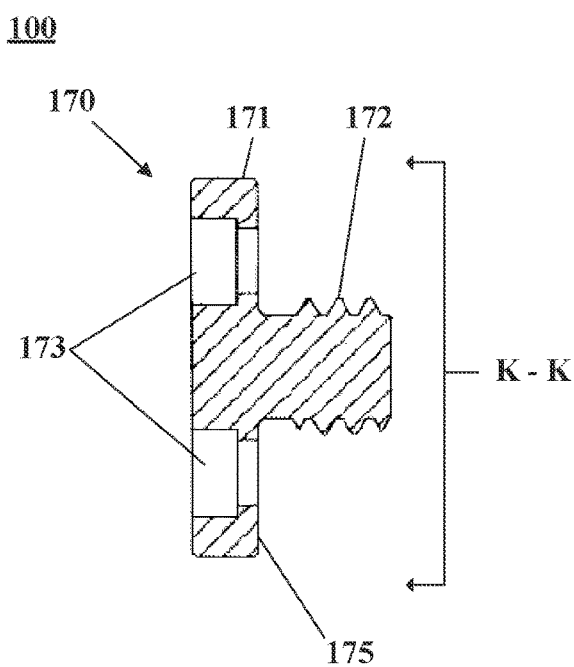
FIG. 7C depicts a cross-sectional view of the stop plate of FIG. 7A along the K-K axis.

FIGS. 7A-7C depict stop plate 170 having stop cap 171 and stop post 172. Stop cap 171 may be welded to stop post 172 through holes 173. Stop post 172 extends from stop cap 171 and is configured to be received in threaded openings 118a,b when the stop cap and the posts 117a,b of end plate 110 are received in gear sleeves 140a,b. In this manner, the engagement between superior surface 175 of stop cap 171 and ledges 146 of gear sleeves 140a,b can set a limit on the distance traveled by end plate 110 while device 100 is in its expanded condition.

Figure 8A:
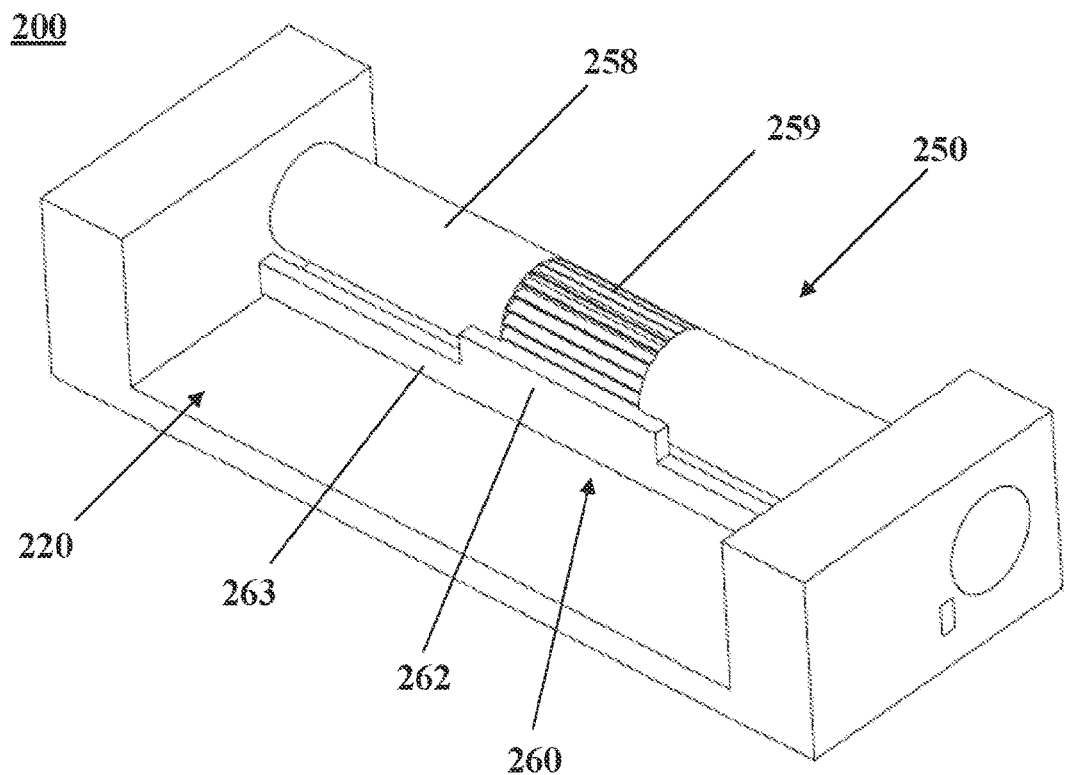
FIG. 8A depicts a schematic isometric view of a portion of a locking mechanism of an expandable device according to another embodiment of the disclosure.
Figure 8B:
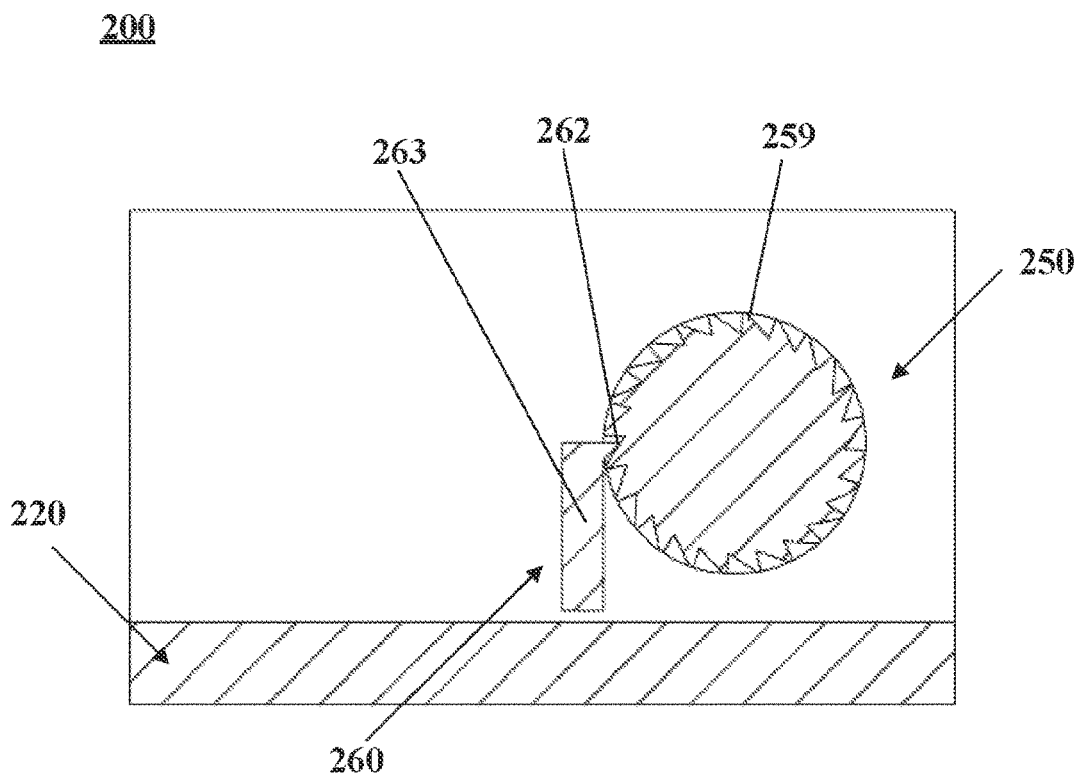
FIG. 8B depicts a cross-sectional view of a component of a locking portion of the expandable device of FIG. 8A.

In an alternative embodiment, the locking mechanism may additionally or alternatively include a pawl to interact with ratchet teeth along the body of the worm gear. FIGS. 8A-8B, depicts a schematic representation of expandable device 200 including each of the features of device 100 except as discussed below. Worm gear 250 includes toothed section 259 located along a central portion of body 258 of the worm gear. Locking mechanism 260 is coupled to body 220 and includes pawl 263 having ratchet tooth 262. The sloped portions of ratchet tooth 262 of locking mechanism 260 engage with the sloped portions of toothed section 259 such that worm gear 250 can be rotated in a first direction, such as a clockwise direction, but the axial portions of the ratchet teeth apply a resistance to the toothed section to prevent the worm gear from rotating in a second, opposite direction. Ratchet tooth 262 can be disengaged from toothed section 259 by either translating or pivoting the pawl 263 of locking mechanism 260 away from worm gear 250. This ratcheting engagement assists in preventing back driving of worm gear 250 and unintentional collapsing of device 200. Although not shown in FIG. 8A, worm gear 250 can include threaded sections, such as threaded sections 157a,b shown in FIGS. 5A-5B, located on either side of toothed section 259. In a further alternative, there can be multiple toothed sections 259 and multiple corresponding pawls 263. In a yet further alternative, toothed section 259 is not located along a central portion of body 258 but rather can be placed along any portion of the body.

Figure 9:
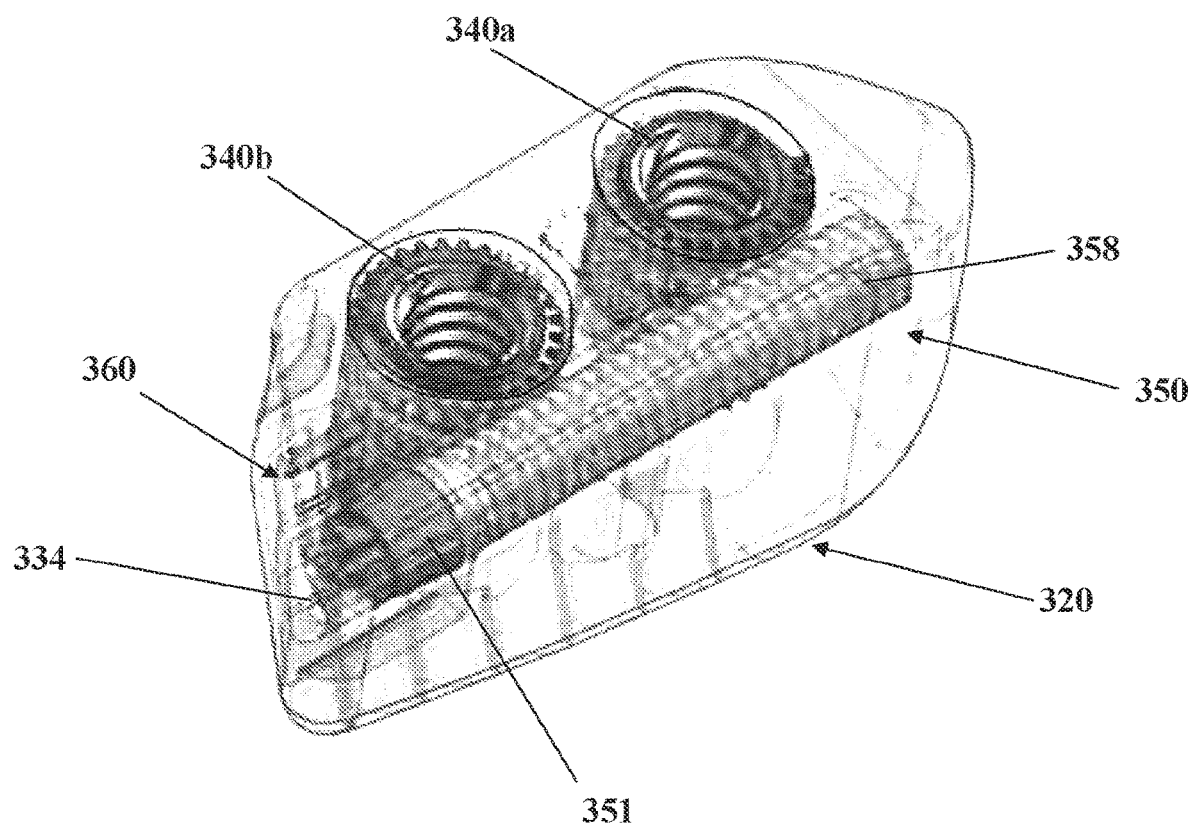
FIG. 9 depicts an isometric view of internal components of an expandable device according to another embodiment of the disclosure.

In a further alternative embodiment, the locking mechanism may instead take the form of a taper lock. For example, FIG. 9 depicts expandable device 300 including each of the features of device 100, 200 except as discussed below. Worm gear 350 includes tapered cap 351 and a threaded body 358 configured to engage with gear sleeves 340a,b. The gear sleeves 340a,b in this embodiment would both be threaded in the same way (i.e., either both right-handed or both left-handed), and the thread sections of the worm gear 350 would also be threaded in the same way as one another, or the body 358 could be entirely threaded, as shown in FIG. 9. Once worm gear 350 is inserted into the bore within body 320 and engaged with gear sleeves 340a,b, locking mechanism 360 is inserted over cap 351 to retain the worm gear 350 within the bore. Opening 334 of locking mechanism 360 is shaped to have a more acute taper than the taper of cap 351, however the opening is proximally offset from the cap such that the cap would have to travel a proximal distance in order to mate with the opening. In this manner, once worm gear 350 has been rotated to expand device 100 to a desired height, downward pressure on the expanded end plate (not shown) would tend to cause the gear sleeves 340a,b to rotate backwards towards an unexpanded position. Moreover, since both gear sleeves are threaded in the same direction, the backwards rotation would result in the teeth of the gear sleeves acting like pinions tending to push the worm gear 350 like a rack back in the proximal direction. In an alternative embodiment, a compression spring may be located at the distal end of the worm gear 350 to bias the worm gear in the proximal direction. As a result, frictional force will develop between cap 351 and tapered opening 334 that will prevent back driving of the worm gear 350. To further expand or collapse device 100, an actuation mechanism (not shown) is inserted within cap 351 and a slight distal force is applied to disengage cap 351 and opening 334 such that worm gear 350 is freely rotatable.

Figure 10:
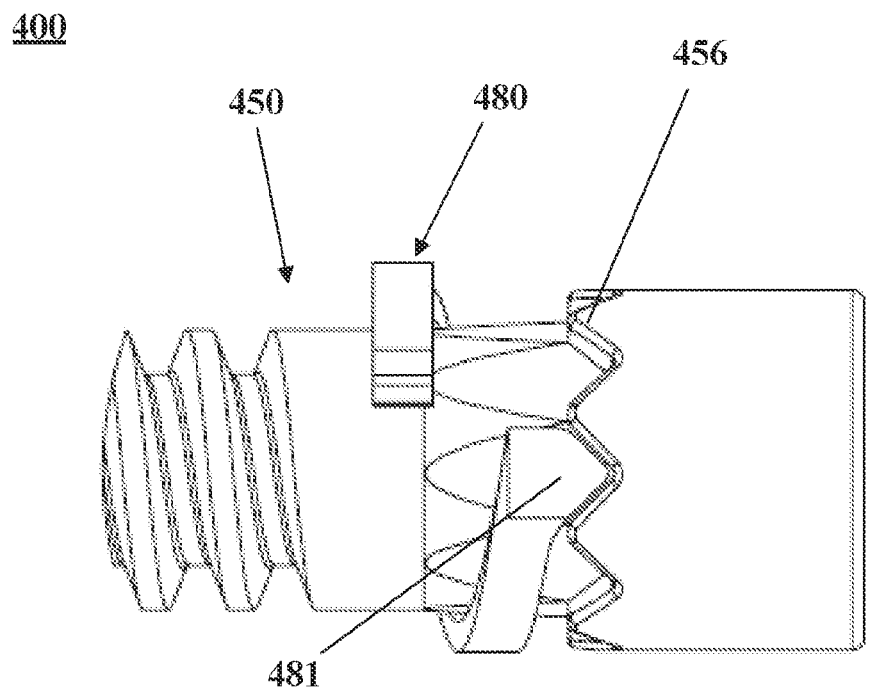
FIG. 10 depicts an enlarged isometric view of a component of a locking mechanism of an expandable device according to another embodiment of the disclosure.

In a yet further alternative embodiment, the locking mechanism can be a clutch plate interacting with a spring. For example, FIG. 10 depicts expandable device 400 including each of the features of device 100, 200, 300 except as discussed below. Spring 480 includes a tooth 481 engaged with ratchet teeth 456 connected to the worm gear 450 such that a spring force is applied to the ratchet teeth. In this manner, spring 480 acts as a passive locking mechanism for worm gear 450, as rotation of the worm gear requires overcoming the force of spring 480 to turn the worm gear. Ratchet teeth 456 may include two sloped portions rather than one sloped portion and one axial portion (as in ratchet teeth 162 of locking mechanism 160 shown in FIGS. 6A-6B). Thus, worm gear 450 may be rotated in either direction by overcoming the locking force applied by the spring 480.

Figure 11:
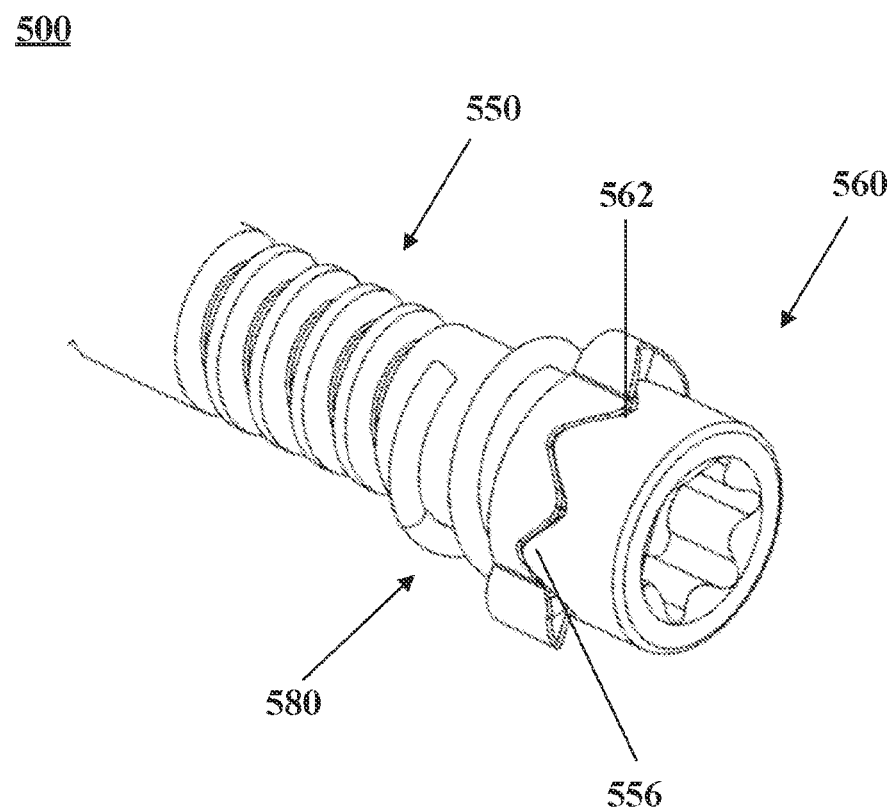
FIG. 11 depicts an enlarged isometric view of a component of a locking mechanism of an expandable device according to another embodiment of the disclosure.

Alternatively, rather than the spring having its own tooth for directly interacting with the ratchet teeth of the worm gear, the locking mechanism can include a lock washer biased by the spring into engagement with the ratchet teeth of the worm gear, where the lock washer includes one or more corresponding teeth for engaging the ratchet teeth. For example, FIG. 11 depicts expandable device 500 including each of the features of device 100, 200, 300, 400 except as discussed below. Locking mechanism 560, in the form of a lock washer, includes ratchet teeth 562 shaped to engage the ratchet teeth 556 of worm gear 550. Like ratchet teeth 456 of FIG. 10, ratchet teeth 556 and 562 of FIG. 11 may include two sloped portions rather than one sloped portion and one axial portion, so as to permit worm gear 550 to be rotated in either direction by overcoming the locking force of the spring 580 pressing ratchet teeth 562 of the locking mechanism 560 against ratchet teeth 556 of the worm gear 550.

In further alternatives (not shown), the ratchet teeth of the locking mechanisms of FIGS. 10 and 11 may include one sloped portion and one axial portion, so that worm gear may only be rotated in one direction without disengaging the locking mechanism.

Figure 12:
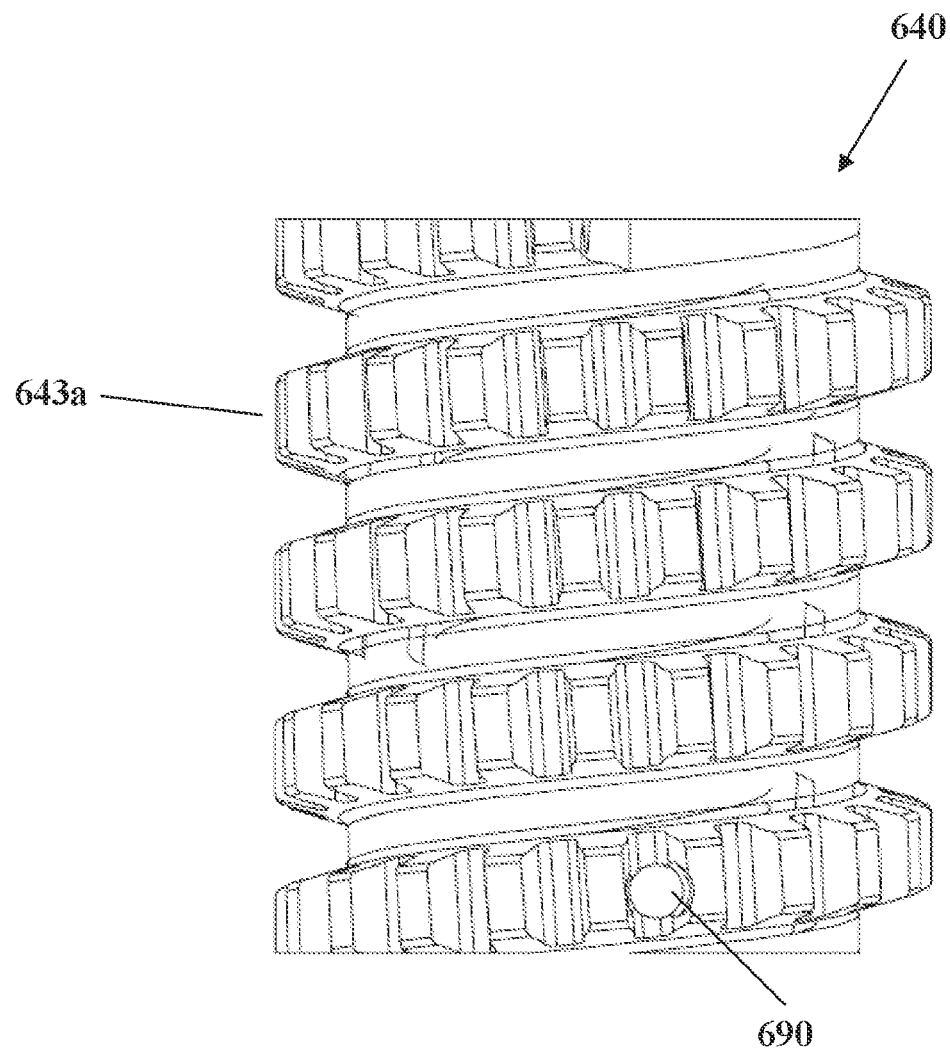
FIG. 12 depicts an isometric view of a component of an expandable device according to another embodiment of the disclosure.

In an alternative embodiment, overexpansion of the end plate can be prevented by an interference object associated with one or more of the gear sleeves. For example, FIG. 12 depicts expandable device 600 including each of the features of device 100, 200, 300, 400, 500 except, rather than stop plate 170 shown in FIG. 1 setting a limit on expansion of device 100, an interference object in the form of a ball bearing 690 can be positioned in gear teeth 643a to stop gear sleeve 640 from further rotation when that object contacts the engaging threads of the worm gear.

Figure 13:
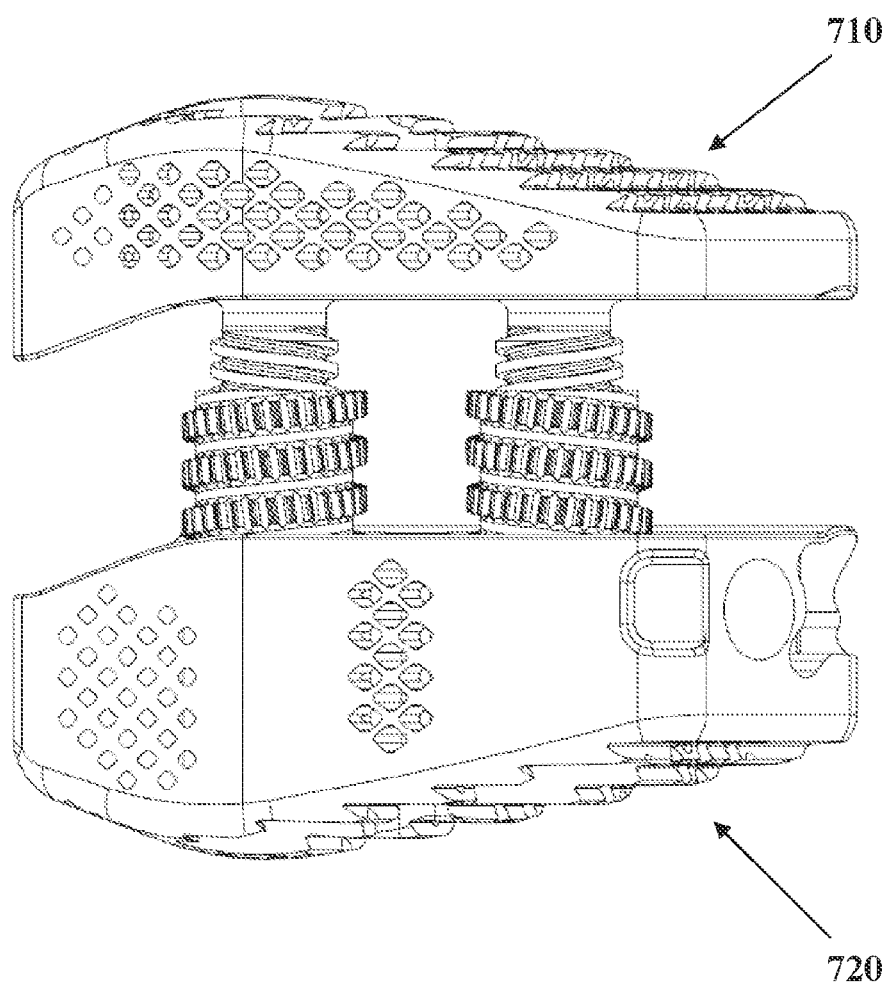
FIG. 13 depicts an isometric view of an expandable device according to another embodiment of the disclosure.

In a further alternative embodiment, the end plate and body can have an alternative shape. FIG. 13 depicts expandable device 700 including each of the features of device 100, 200, 300, 400, 500, 600 except end plate 710 and body 720 both have a superior and inferior surface sloping outwardly from the proximal end towards the distal end. Such sloping surfaces may help with lordotic correction of the adjacent vertebral bodies.

Figure 14:
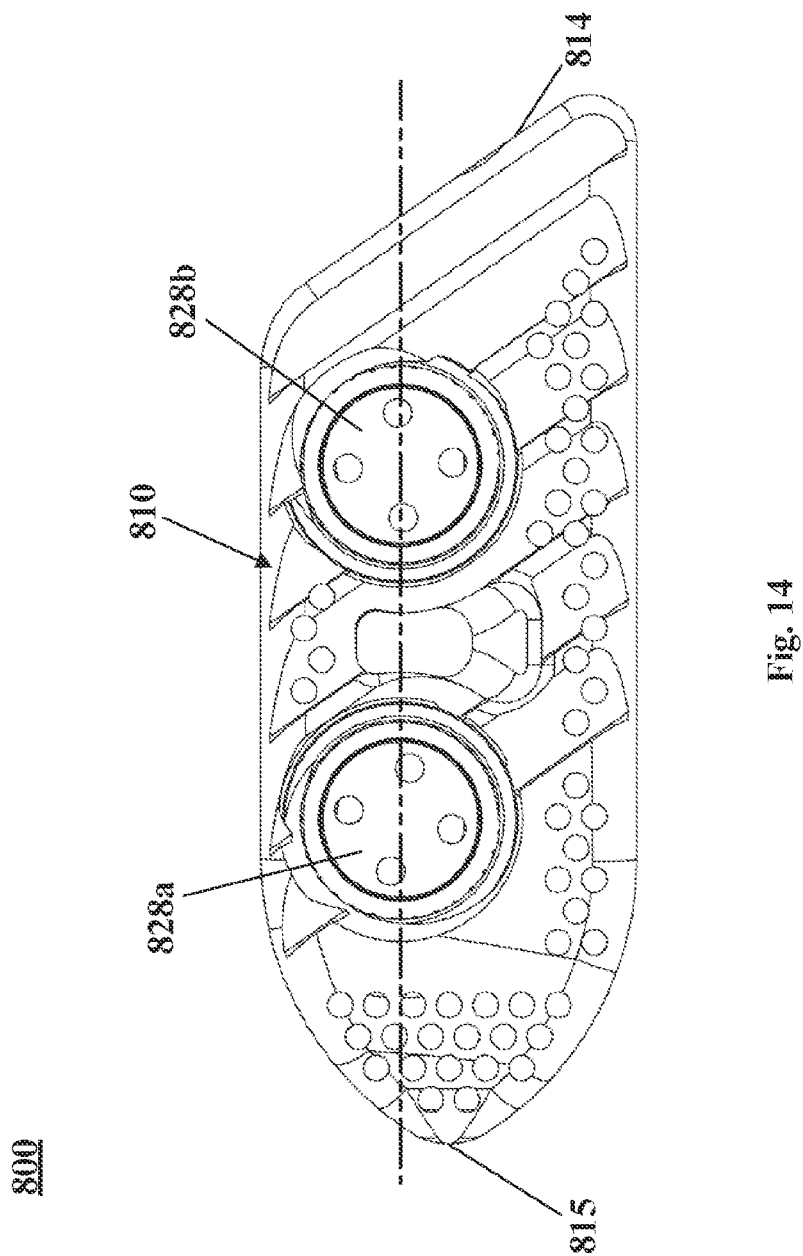
FIG. 14 depicts a top view of an expandable device according to another embodiment of the disclosure.
Figure 15:
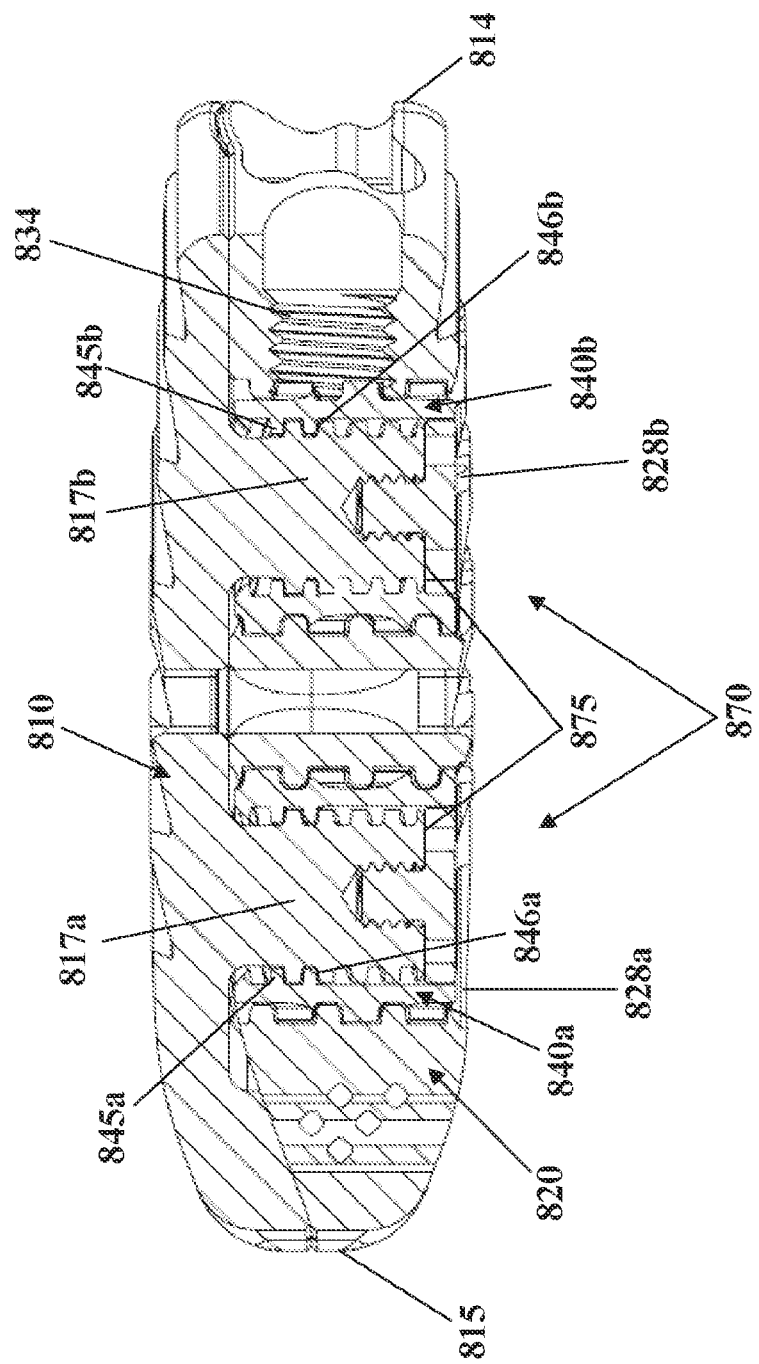
FIG. 15 depicts a cross-sectional elevation view of the expandable device of FIG. 14 in a collapsed condition.

In a yet further alternative embodiment, FIGS. 14-16 depict expandable device 800, which may include any of the features of device 100, 200, 300, 400, 500, 600, and/or 700, except that proximal end 814 of end plate 810 and body 820 may be angled obliquely relative to the longitudinal dimension of the device 800. In this manner, device 800 may be inserted into a patient with proximal end 814 offset from and angled with respect to the longitudinal axis of the inserter. In that manner, device 800 may be better suited in a transforaminal lumbar interbody fusion (TLIF) procedure, whereas the straighter embodiments depicted above may be more suitable in a posterior lumbar interbody fusion (PLIF) procedure or a lateral approach, for example. In alternative embodiments, the angled surface along proximal end 814 of expandable device 80 may be angled in an opposite direction to that displayed in FIG. 14.

Although the above embodiments involve the end plate having two posts, in other embodiments, the end plate may have more or fewer than two posts. Further, the number of gear sleeves and thread sections on the worm gear may correspond to the number of posts (e.g., three gear sleeves and three threaded sections on the worm gear where the end plate has three posts).

The expandable device may be constructed, in whole or in part, from one or more biocompatible metals, such as but not limited to any one of or any combination of titanium and its alloys, stainless steel and its alloys, magnesium and its alloys, cobalt and its alloys including a cobalt chrome alloy, nickel and its alloys, silver, tantalum, and niobium. It is also contemplated that any part of the expandable device may be made from one or more biocompatible polymers, such as but not limited to any one of or any combination of polyethylene (PE) and variations thereof, polyetheretherketone (PEEK), polyetherketone (PEK), acrylonitrile butadiene styrene (ABS), silicone, and cross-linked polymers.

With reference to FIGS. 14-15, methods of using expandable device 800 will now be described, however expandable devices 100, 200, 300, 400, 500, 600, 700 may be operated via similar methods, except as described below. As shown in FIG. 14, device 800 is depicted in its collapsed condition and ready to be implanted within an intervertebral space between two adjacent vertebrae. An inserter (not shown) may first be engaged with threaded opening 834 to assist in manipulation and insertion of device 800 within the intervertebral space, leading with distal end 815. The inserter may be disengaged after implanting device 800 or may stay engaged.

Once device 800 has been implanted, a first actuation mechanism (not shown) can be inserted into opening 852 of worm gear 850 such that rotation of the first actuation mechanism in a first direction (e.g., a clockwise direction) correspondingly rotates the worm gear within bore 832 of body 820 while the longitudinal position of the worm gear 850 is maintained by pin 890 received in indent 853 of the worm gear. Rotation of worm gear 850 within bore 832 rotates the sloped portions of ratchet teeth 856 against the sloped portions of extended ratchet tooth 861 and ratchet teeth 862 of locking mechanism 860. Additionally, rotation of worm gear 850 rotates gear sleeves 840a,b through the engagement between gear teeth 843a,b and thread sections 857a,b. Rotation of worm gear 850 includes overcoming a slight resistance from spring 880 pressing locking mechanism 860 against cap 851 of the worm gear.

Gear sleeves 840a,b are rotated within threaded openings 828a,b of body 820 through the engagement between exterior threads 844a,b of the gear sleeves and the interior threads of the threaded openings of the body. Rotation of gear sleeves 840a,b within threaded openings 828a,b additionally translates the gear sleeves in a superior direction. Further, rotation of gear sleeves 840a,b causes the gear sleeves to rotate about posts 817a,b such that the engagement between threaded section 845a,b of channel 848a,b of the gear sleeves and the exterior threads of the posts translates the posts in a superior direction. As such, rotation of worm gear 850 simultaneously rotates gear sleeves 840a,b about posts 817a,b while also translating both the gear sleeves and the posts in a superior direction.

Translation of posts 817a,b is limited by the contact between superior surface 875 of stop plate 870 and ledges 846a,b within second portion 847a,b of gear sleeves 840a,b. In this manner, rotation of worm gear 850 translates both gear sleeves 840a,b and end plate 810 in a superior direction until a desired height, or where a maximum height is reached through the engagement between stop plate 870 and the gear sleeves.

Once device 800 has finished expanding, locking mechanism 860 locks the position of worm gear 850 and end plate 810 in place. That is, locking mechanism 860 cannot rotate towards the unexpanded position due to the engagement between extension 863 and extended ratchet tooth 861 of locking mechanism 860 with the respective first portion 835 and second portion 836 of first section 833 of bore 832. Therefore, worm gear 850 is prevented from rotating in a second counter-clockwise direction through the engagement and resistance force of the axial portions of extended ratchet tooth 861 and ratchet teeth 862 of the locking mechanism against the axial portions of ratchet teeth 856 of the worm gear. End plate 810 cannot translate without counter-clockwise rotation of worm gear 850 and corresponding rotation of gear sleeves 840a,b, so locking mechanism 860 prevents the worm gear from rotating in the counter-clockwise direction, thereby locking the position of end plate 810 and preventing unintentional collapse of device 800. In this manner, device 800 can maintain an expanded condition when a desired height of end plate 810 is reached without a separate step of locking the position of the end plate (e.g., through the use of a set screw, or the like). This increases the efficiency of the surgery and decreases the chance of complications arising.

To transition device 800 from the expanded condition to the collapsed condition, a second actuation mechanism (not shown), such as a pin provided by the inserter, can enter first or second portions 835, 836 to distally push extension 863 or extended ratchet tooth 861 of locking mechanism 860 distally into body 820. That second actuation mechanism must overcome the force of spring 880 until extended ratchet tooth 861 and ratchet teeth 862 of the locking mechanism disengage from ratchet teeth 856 of worm gear 850. In a preferred embodiment, the actuating mechanism engages the proximal end 864 of extension 863 of locking mechanism 860 to disengage ratchet teeth 856 of worm gear 850 from ratchet teeth 862 of locking mechanism 860. While maintaining the second actuation mechanism in this position, such that locking mechanism 860 and worm gear 850 do not re-engage, the first actuation mechanism may rotate the worm gear counter-clockwise, correspondingly rotating gear sleeves 840a,b within body 820 and posts 817a,b to inferiorly translate the gear sleeves and end plate 810 until a desired height is reached (e.g., a collapsed condition).

With reference to FIGS. 8A-8B, device 200 may transition from the expanded condition to the collapsed condition by at least one of translating or pivoting pawl 263 of locking mechanism 260 away from worm gear 250 to disengage ratchet tooth 262 of the locking mechanism 260 from ratchet teeth 259 of the worm gear. Once locking mechanism 260 and worm gear 250 are disengaged, the worm gear can be rotated in a counter-clockwise direction to collapse device 200.

With reference to FIGS. 9A-9B, the position of device 300 and worm gear 350 may be locked through the engagement between tapered cap 351 and opening 334 of locking mechanism 360. Opening 334 is configured to have a taper angle that is more acute than a taper angle of cap 351 such that, once device 300 is at a desired expanded condition, excess back driving of worm gear 350 would be prevented from the resistance, frictional force of the cap being mated with the opening. Worm gear 350 can be further rotated to further expand or collapse device 300 by an actuation mechanism (not shown) applying a slight distal force on cap 351 to disengage cap 351 from opening 334.

With reference to FIG. 10, spring 480 passively locks the position of worm gear 450 through a spring force being applied to the engagement between tooth 481 and ratchet teeth 456 of the worm gear. In this manner, further rotation of worm gear 450 requires a rotational force to be applied to cap 451 greater than the spring force from spring 480. Similarly, with reference to FIG. 11, spring 580 passively locks the position of worm gear 550 through a spring force being applied to the engagement between ratchet teeth 562 of locking mechanism 560 and ratchet teeth 556 of the worm gear.

With reference to FIG. 12, overexpansion of device 600 can be prevented through the use of ball bearing 690 being positioned within gear teeth 643a to prevent further rotation of gear sleeve 640 and, in turn, further superior translation of the end plate (not shown).

Although the disclosure herein has been described with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present disclosure as defined by the appended claims.

The invention claimed is:

1. An expandable device comprising:
   a body defining a bore;
   a shaft received in the bore of the body;
   an end plate coupled to the body, wherein rotation of the shaft translates the end plate with respect to the body; and
   a locking mechanism engaged with the shaft so as to permit the shaft to rotate in a first direction and apply a resistance force to resist the shaft when attempting to rotate in a second direction,
   wherein the shaft includes a cap at an end of a body of the shaft, the cap configured to engage the locking mechanism, and wherein the cap has a first set of ratchet teeth and the locking mechanism has a second set of ratchet teeth configured to engage the first set of ratchet teeth, the second set of ratchet teeth applying the resistance force to the first set of ratchet teeth.

2. The expandable device of claim 1, wherein at least one of the end plate and the body includes a textured surface.

3. The expandable device of claim 1, wherein at least one of the end plate and the body includes a plurality of pores.

4. The expandable device of claim 1, wherein the end plate defines an opening and the body defines an opening, the opening of the end plate being in communication with the opening of the body.

5. The expandable device of claim 1, wherein the body defines a first opening transverse to the bore, the device further comprising a first gear sleeve threadably received in the first opening of the body.

6. The expandable device of claim 5, wherein the first gear sleeve defines a channel, the end plate including a first post received in the channel of the first gear sleeve, wherein the first gear sleeve includes gear teeth, the shaft having a first threaded section engaged with the gear teeth.

7. The expandable device of claim 6, wherein:
the body includes a second opening;
the expandable device further comprises a second gear sleeve received in the second opening, the second gear sleeve having gear teeth and defining a channel therethrough;
the end plate has a second post received in the channel of the second gear sleeve; and
the shaft has a second threaded section engaged with the gear teeth of the second gear sleeve.

8. The expandable device of claim 5, further comprising a ball bearing configured to engage with gear teeth of the first gear sleeve.

9. The expandable device of claim 1, further comprising a pin, wherein the body defines a hole configured to receive the pin, wherein the shaft defines an indent configured to engage with the pin such that the shaft is axially fixed to the body.

10. The expandable device of claim 1, further comprising a spring applying a spring force to the locking mechanism.

11. The expandable device of claim 1, wherein the cap is tapered with a first taper angle and the locking mechanism is tapered with a second taper angle, the second taper angle being more acute than the first taper angle such that the locking mechanism applies the resistance force to the cap when the locking mechanism is engaged to the cap.

12. The expandable device of claim 1, wherein the bore includes a first section and a second section, the first section configured to receive the cap and the second section configured to receive the body of the shaft, the first section having a first diameter and the second section having a second diameter, the first diameter being larger than the second diameter, wherein the locking mechanism includes an extension and the first section includes a first portion radially extending from the first section, the first portion configured to receive the extension such that the locking mechanism is rotationally fixed within the first section.

13. The expandable device of claim 1, wherein the locking mechanism includes a pawl having a ratchet tooth configured to engage teeth on the shaft.

14. An expandable device comprising:
a body defining a bore and a first opening transverse to the bore;
a shaft received in the bore of the body;
a first gear sleeve received in the first opening and defining a channel, the first gear sleeve having a stopping surface within the channel;
an end plate having a first post received in the channel of the first gear sleeve; and
a stop plate engaged with the first post and received in the channel, wherein rotation of the shaft translates the end plate from a first position in which the stop plate is spaced from the stopping surface to a second position in which the stop plate abuts the stopping surface, thereby defining a limit of translation of the end plate.

15. The expandable device of claim 14, wherein the first post of the end plate defines a threaded opening and the stop plate includes a post, the post of the stop plate received in the threaded opening of the first post of the end plate.

16. The expandable device of claim 14, wherein the stop plate defines a hole radially distant from an axis defined by the first post and configured to receive a set screw.

17. The expandable device of claim 14, wherein the channel of the first gear sleeve defines a first threaded section configured to receive the post of the end plate and a second section configured to receive the stop plate.

18. The expandable device of claim 17, wherein the stopping structure lies between the first threaded section and the second section.

19. The expandable device of claim 14, wherein the first gear sleeve includes gear teeth, the shaft having a first threaded section engaged with the gear teeth.

20. The expandable device of claim 14, further comprising a pin, wherein the body defines a hole configured to receive the pin, wherein the shaft defines an indent configured to engage with the pin such that the shaft is axially fixed to the body.

* * * * *